United States Patent [19]
Lee

[11] Patent Number: 5,639,777
[45] Date of Patent: Jun. 17, 1997

[54] 1,4,5-TRIPHENYL PYRAZOLYL COMPOUNDS FOR THE TREATMENT OF INFLAMMATION AND INFLAMMATION-RELATED DISORDERS

[75] Inventor: Len F. Lee, St. Charles, Mo.

[73] Assignee: G.D. Searle & Co., Skokie, Ill.

[21] Appl. No.: 648,118

[22] PCT Filed: Nov. 14, 1994

[86] PCT No.: PCT/US94/12721

§ 371 Date: May 21, 1996

§ 102(e) Date: May 21, 1996

[87] PCT Pub. No.: WO95/15317

PCT Pub. Date: Jun. 8, 1995

Related U.S. Application Data

[63] Continuation-in-part of Ser. No. 161,004, Nov. 30, 1993, Pat. No. 5,401,765.

[51] Int. Cl.$^6$ ............... A61K 31/415; C07D 231/12; C07D 231/14
[52] U.S. Cl. ............... 514/406; 548/375.1; 548/377.1
[58] Field of Search ............... 548/375.1, 377.1; 514/406

[56] References Cited

U.S. PATENT DOCUMENTS 3,984,431  10/1976  Guérémy et al. .
5,134,142   7/1992  Matauo et al. .
5,466,823  11/1995  Talley et al. ............ 548/377.1

OTHER PUBLICATIONS

J. Mizoule et al, *Arch. int. Pharmacodyn.*, 238, 305–322 (1979).
H. House et al, *J. Amer. Chem. Soc.*, 79, 2490–2495 (1957).
J. Grimshaw et al., *J. Chem. Soc. Perkin. Trans.* 1, 2096–2099 (1977).
J. Wilshire, *Aust. J. Chem.*, 27, 2041–2045 (1974).
H. House et al, *J. Amer. Chem. Soc.*, 83, 979–983 (1961).
M. Weissenfels et al, *J. Prakt. Chem.*, 315, 873–880 (1973).
V. Szabó et al, *Acta Chim. Acad. Sci. Hung.*, 98, 457–462 (1979).
H. Gnichtel et al, *Liebigs Ann. Chem.*, 589–591 (1989).
I. Gambhir et al., *J. Org. Chem.*, 27, 1899–1901 (1962).
H. Biere, *Arch. Pharm.*, 316, 608–616 (1983).

*Primary Examiner*—Robert W. Ramsuer
*Attorney, Agent, or Firm*—Joseph W. Bulock

[57] ABSTRACT

A class of 1,4,5-triphenyl pyrazoles is described for the treatment of inflammation, including treatment of pain and disorders such as arthritis. Compounds of particular interest are of Formula II

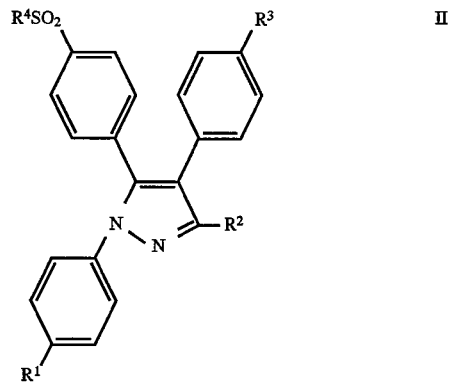

wherein $R^1$ is selected from the group hydrido, halo, alkyl, alkylthio, alkylsulfinyl, alkylsulfonyl, nitro, amino, N-monoalkylamino, N,N-dialkylamino, acylamino, acylaminoalkyl, haloalkyl, hydroxy and alkoxy; wherein $R^2$ is selected from hydrido, alkyl, cyano and haloalkyl; wherein $R^3$ is selected from the group hydrido, halo, alkyl, alkylthio, alkylsulfinyl, alkylsulfonyl, nitro, amino, N-monoalkylamino, N,N-dialkylamino, acylamino, acylaminoalkyl, haloalkyl, hydroxy and alkoxy; and wherein $R^4$ is alkyl or amino; or a pharmaceutically-acceptable salt thereof.

22 Claims, No Drawings

1,4,5-TRIPHENYL PYRAZOLYL COMPOUNDS FOR THE TREATMENT OF INFLAMMATION AND INFLAMMATION-RELATED DISORDERS

RELATED CASE

This is an application under 35 USC §371 of international application PCT/US94/12721, with an international filing date of Nov. 14, 1994, which is a continuation-in-part of U.S. patent application Ser. No. 08/161,004, filed Nov. 30, 1993, now issued as U.S. Pat. No. 5,401,765.

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. A popular current alternative to NSAIDs is the use of corticosteroids, which have even more drastic side effects, especially when long term therapy is involved.

Several families of pyrazole-containing compounds have been described as having anti-inflammatory activity. U.S. Pat. No. 5,134,142 to Matsuo et al describes 1,5-diarylpyrazoles, and specifically 1-(4-fluorophenyl)-5-[(4-methylsulfonyl)phenyl]-3-trifluoromethyl-1H-pyrazole, as having anti-inflammatory activity.

U.S. Pat. No. 3,984,431 to Gueremy et al describes derivatives of pyrazole-5-acetic acid as having anti-inflammatory action. Isofezolac (1,3,4-triphenyl-1H-pyrazole-5-acetic acid) is specifically described. 1,3,4-Triphenyl-5-(chloromethyl)-1H-pyrazole is described as an intermediate in the formation of the above mentioned derivatives. Isofezolac has been found to be as ulcerogenic as other common anti-inflammatory agents [J. Mizoule et al, Arch. int. Pharmacodyn., 238, 305 (1979)].

Little pharmaceutical activity has been described for 1,4,5-triphenyl-1H-pyrazolyl compounds. The rearrangement of epoxyketones has been observed to produce 1,4,5-triphenyl-1H-pyrazole [H. House et al, J. Amer. Chem. Soc., 79, 2490 (1957)]. Photochemical reactions of 4-(2-chlorophenyl)-1,5-diphenyl-1H-pyrazole and of 1,4,5-triphenyl-1H-pyrazole have been described [J. Grimshaw et al, J. Chem. Soc. Perkin. Trans. 1, 2096 (1977)]. The synthesis of a series of 1-aryl-4,5-diphenyl-1H-pyrazoles and a series of 1-aryl-3,4-diphenyl-1H-pyrazoles by reacting 2-phenylacrylophenone and arylhydrazines has been described [J. Wilshire, Aust. J. Chem., 27, 2041 (1974)]. Specifically 1-(4-methylphenyl)-4,5-diphenyl-1H-pyrazole is described. The rearrangement of epoxyphenylpropiophenone has been observed to produce 1-phenyl-4,5-substitutedphenyl-1-H-pyrazoles, and specifically 1-phenyl-4,5-di(chlorophenyl)-1H-pyrazole [H. House et al, J. Amer. Chem. Soc., 83, 979 (1961)]. Triarylpyrazole compounds are prepared by reacting thioketoaldehydes and phenylhydrazines [M. Weissenfels et al, J. Prakt. Chem., 315, 873 (1973)] and specifically 4,5-bis(4-methoxyphenyl)-1-phenyl-1H-pyrazole. The reaction of phenylhydrazines with isoflavonoids to yield pyrazole compounds, such as 2-(1,4-diphenyl-1H-pyrazol-5-yl)-phenol has been described [V. Szabó et al, Acta Chim. Acad. Sci, Hung., 98, 457 (1979)].

The reaction of benzoin phenylhydrazone with aldehydes to produce 3-alkyl-1,4,5-triphenyl-1H-pyrazoles is described [H. Gnichtel et al, Liebigs Ann. Chem., 589 (1989)]. Specifically, 3-methyl-1,4,5-triphenyl-1H-pyrazole is described. The reaction of dinitrophenyl diketone derivatives with hydrazines has been studied, and 4-(2,4-dinitro)phenyl-1-(4-methylphenyl)-5-phenyl-3-methyl-1H-pyrazole has been described [I. Gambhir et al, J. Org. Chem., 27, 1899 (1962)].

1,4,5-Triphenyl-3-bromomethyl-1H-pyrazole is described as an intermediate in the synthesis of 1,4,5-triphenyl-1H-pyrazole-3-ethanoic acid, which is a potential anti-inflammatory agent [H. Biere, Arch, Pharm., 316, 608 (1983)].

DESCRIPTION OF THE INVENTION

A class of compounds useful in treating inflammation-related disorders is defined by Formula I:

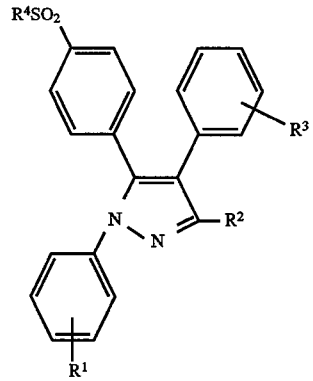

wherein $R^1$ is one or more radicals independently selected from the group hydrido, halo, alkyl, alkylthio, alkylsulfinyl, alkylsulfonyl, nitro, amino, N-monoalkylamino, N,N-dialkylamino, acylamino, acylaminoalkyl, haloalkyl, hydroxy and alkoxy; wherein $R^2$ is selected from hydrido, alkyl, cyano and haloalkyl; wherein $R^3$ is one or more radicals independently selected from the group hydrido, halo, alkyl, alkylthio, alkylsulfinyl, alkylsulfonyl, nitro, amino, N-monoalkylamino, N,N-dialkylamino, acylamino, acylaminoalkyl, haloalkyl, hydroxy and alkoxy; and wherein $R^4$ is alkyl or amino; or a pharmaceutically-acceptable salt thereof.

Compounds of Formula I would be useful for the treatment of inflammation in a subject, and for treatment of other inflammation-associated disorders, such as an analgesic in the treatment of pain and headaches, or as an antipyretic for the treatment of fever. For example, compounds of Formula I would be useful to treat arthritis, including but not limited to rheumatoid arthritis, spondyloarthropathies, gouty arthritis, systemic lupus erythematosus, osteoarthritis and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as anti-inflammatory agents, such as for the treatment of arthritis, with the additional benefit of having significantly less harmful side effects.

A preferred class of compounds consists of those compounds of Formula I wherein $R^1$ is one or more radicals independently selected from the group hydrido, halo, lower alkyl, lower alkylthio, lower alkylsulfinyl, lower alkylsulfonyl, nitro, amino, N-monoalkylamino, N,N-dialkylamino, acylamino, acylaminoalkyl, lower haloalkyl, hydroxy and lower alkoxy; wherein $R^2$ is selected from hydrido, lower alkyl, cyano and lower haloalkyl; wherein $R^3$ is one or more radicals independently selected from the group hydrido, halo, lower alkyl, lower alkylthio, lower alkylsulfinyl, lower alkylsulfonyl, nitro, amino, N-monoalkylamino, N,N-dialkylamino, acylamino, acylaminoalkyl, lower haloalkyl, hydroxy and lower alkoxy; and wherein $R^4$ is lower alkyl or amino; or a pharmaceutically-acceptable salt thereof.

A class of compounds of particular interest consists of those compounds of Formula I wherein $R^1$ is one or more groups independently selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; wherein $R^2$ is selected from hydrido, cyano, methyl, ethyl, propyl, trifluoromethyl, difluorochloromethyl, difluoromethyl, pentafluoroethyl and heptafluoropropyl; wherein $R^3$ is one or more groups independently selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; and wherein $R^4$ is methyl or amino; or a pharmaceutically-acceptable salt thereof.

A family of specific compounds of particular interest within Formula I consists of compounds and pharmaceutically-acceptable salts thereof as follows:

4-(4-fluorophenyl)-5-[4-(methylsulfonyl)phenyl]-1-phenyl-3-(trifluoromethyl)-1H-pyrazole;

4-(4-chlorophenyl)-5-[4-(methylsulfonyl)phenyl]-1-phenyl-3-(trifluoromethyl)-1H-pyrazole;

4-(4-bromophenyl)-5-[4-(methylsulfonyl)phenyl]-1-phenyl-3-(trifluoromethyl)-1H-pyrazole;

4-(4-iodophenyl)-5-[4-(methylsulfonyl)phenyl]-1-phenyl-3-(trifluoromethyl)-1H-pyrazole;

4-(2-fluorophenyl)-5-[4-(methylsulfonyl)phenyl]-1-phenyl-3-(trifluoromethyl)-1H-pyrazole;

4-(2-chlorophenyl)-5-[4-(methylsulfonyl)phenyl]-1-phenyl-3-(trifluoromethyl)-1H-pyrazole;

4-(2,4-difluorophenyl)-5-[4-(methylsulfonyl)phenyl]-1-phenyl-3-(trifluoromethyl)-1H-pyrazole;

4-(2,4-dichlorophenyl)-5-[4-(methylsulfonyl)phenyl]-1-phenyl-3-(trifluoromethyl)-1H-pyrazole;

5-[4-(methylsulfonyl)phenyl]-1,4-diphenyl-3-(trifluoromethyl)-1H-pyrazole;

4-(4-methylphenyl)-5-[4-(methylsulfonyl)phenyl]-1-phenyl-3-(trifluoromethyl)-1H-pyrazole;

4-(4-ethylphenyl)-5-[4-(methylsulfonyl)phenyl]-1-phenyl-3-(trifluoromethyl)-1H-pyrazole;

4-(4-tert-butylphenyl)-5-[4-(methylsulfonyl)phenyl]-1-phenyl-3-(trifluoromethyl)-1H-pyrazole;

4-(4-methylthiophenyl)-5-[4-(methylsulfonyl)phenyl]-1-phenyl-3-(trifluoromethyl)-1H-pyrazole;

4-(4-methylsulfinylphenyl)-5-[4-(methylsulfonyl)phenyl]-1-phenyl-3-(trifluoromethyl)-1H-pyrazole;

4,5-[4-(methylsulfonyl)phenyl]-1-phenyl-3-(trifluoromethyl)-1H-pyrazole;

4-(4-hydroxyphenyl)-5-[4-(methylsulfonyl) phenyl]-1-phenyl-3-(trifluoromethyl)-1H-pyrazole;

4-(4-methoxyphenyl)-5-[4-(methylsulfonyl) phenyl]-1-phenyl-3-(trifluoromethyl)-1H-pyrazole;

4-(4-nitrophenyl)-5-[4-(methylsulfonyl) phenyl]-1-phenyl-3-(trifluoromethyl)-1H-pyrazole;

4-(4-aminophenyl)-5-[4-(methylsulfonyl) phenyl]-1-phenyl-3-(trifluoromethyl)-1H-pyrazole;

4-(4-N-methylaminophenyl)-5-[4-(methylsulfonyl)phenyl]-1-phenyl-3-(trifluoromethyl)-1H-pyrazole;

4-(4-N,N-dimethylaminophenyl)-5-[4-(methylsulfonyl)phenyl]-1-phenyl-3-(trifluoromethyl)-1H-pyrazole;

4-(4-trifluoromethylphenyl)-5-[4-(methylsulfonyl)phenyl]-1-phenyl-3-(trifluoromethyl)-1H-pyrazole;

4-(4-acetamidophenyl)-5-[4-(methylsulfonyl)phenyl]-1-phenyl-3-(trifluoromethyl)-1H-pyrazole;

4-(4-[N-acetylamino]methylphenyl)-5-[4-(methylsulfonyl)phenyl]-1-phenyl-3-(trifluoromethyl)-1H-pyrazole;

1-(4-fluorophenyl)-5-[4-(methylsulfonyl)phenyl]-4-phenyl-3-(trifluoromethyl)-1H-pyrazole;

1-(4-chlorophenyl)-5-[4-(methylsulfonyl)phenyl]-4-phenyl-3-(trifluoromethyl)-1H-pyrazole;

1-(4-bromophenyl)-5-[4-(methylsulfonyl)phenyl]-4-phenyl-3-(trifluoromethyl)-1H-pyrazole;

1-(4-iodophenyl)-5-[4-(methylsulfonyl)phenyl]-4-phenyl-3-(trifluoromethyl)-1H-pyrazole;

1-(4-methylphenyl)-5-[4-(methylsulfonyl)phenyl]-4-phenyl-3-(trifluoromethyl)-1H-pyrazole;

1-(4-ethylphenyl)-5-[4-(methylsulfonyl)phenyl]-4-phenyl-3-(trifluoromethyl)-1H-pyrazole;

1-(4-tert-butylphenyl)-5-[4-(methylsulfonyl)phenyl]-4-phenyl-3-(trifluoromethyl)-1H-pyrazole;

1-(4-methylthiophenyl)-5-[4-(methyl sulfonyl)phenyl]-4-phenyl-3-(trifluoromethyl)-1H-pyrazole;

1-(4-methylsulfinylphenyl)-5-[4-(methylsulfonyl)phenyl]-4-phenyl-3-(trifluoromethyl)-1H-pyrazole;

1,5-[4-(methylsulfonyl)phenyl]-4-phenyl-3-(trifluoromethyl)-1H-pyrazole;

1-(4-hydroxyphenyl)-5-[4-(methylsulfonyl)phenyl]-4-phenyl-3-(trifluoromethyl)-1H-pyrazole;

1-(4-methoxyphenyl)-5-[4-(methylsulfonyl phenyl]-4-phenyl-3-(trifluoromethyl)-1H-pyrazole;

1-(4-nitrophenyl)-5-[4-(methylsulfonyl)phenyl]-4-phenyl-3-(trifluoromethyl)-1H-pyrazole;

1-(4-aminophenyl)-5-[4-(methylsulfonyl)phenyl]-4-phenyl-3-(trifluoromethyl)-1H-pyrazole;

1-(4-N-methylaminophenyl)-5-[4-(methylsulfonyl)phenyl]-4-phenyl-3-(trifluoromethyl)-1H-pyrazole;

1-(4-N,N-dimethylaminophenyl)-5-[4-(methylsulfonyl)phenyl]-4-phenyl-3-(trifluoromethyl)-1H-pyrazole;

1-(4-trifluoromethylphenyl)-5-[4-(methylsulfonyl)phenyl]-4-phenyl-3-(trifluoromethyl)-1H-pyrazole;

1-(4-acetamidophenyl)-5-[4-(methylsulfonyl)phenyl]-4-phenyl-3-(trifluoromethyl)-1H-pyrazole;

1-(4-[N-acetylamino]methylphenyl)-5-[4-(methylsulfonyl)phenyl]-4-phenyl-3-(trifluoromethyl)-1H-pyrazole;

4-(4-fluorophenyl)-5-[4-(methylsulfonyl)phenyl]-1-phenyl-3-(difluoromethyl)-1H-pyrazole;

4-(4-fluorophenyl)-5-[4-(methylsulfonyl)phenyl]-1-phenyl-3-chlorodifluoromethyl-1H-pyrazole;

4-(4-fluorophenyl)-5-[4-(methylsulfonyl)phenyl]-1-phenyl-3-pentafluoroethyl-1H-pyrazole;

4-(4-fluorophenyl)-5-[4-(methylsulfonyl)phenyl]-1-phenyl-3-heptafluoropropyl-1H-pyrazole;

4-(4-chlorophenyl)-5-[4-(methylsulfonyl)phenyl]-1-phenyl-3-(difluoromethyl)-1H-pyrazole;

4-(4-bromophenyl)-5-[4-(methylsulfonyl)phenyl]-1-phenyl-3-(difluoromethyl)-1H-pyrazole;

4-(4-iodophenyl)-5-[4-(methylsulfonyl)phenyl]-1-phenyl-3-(difluoromethyl)-1H-pyrazole;

4-(2-fluorophenyl)-5-[4-(methylsulfonyl)phenyl]-1-phenyl-3-(difluoromethyl)-1H-pyrazole;

4-(2-chlorophenyl)-5-[4-(methylsulfonyl)phenyl]-1-phenyl-3-(difluoromethyl)-1H-pyrazole;

4-(2,4-difluorophenyl)-5-[4-(methylsulfonyl)phenyl]-1-phenyl-3-(difluoromethyl)-1H-pyrazole;

4-(2,4-dichlorophenyl)-5-[4-(methylsulfonyl)phenyl]-1-phenyl-3-(difluoromethyl)-1H-pyrazole;

5-[4-(methylsulfonyl)phenyl]-1,4-diphenyl-3-(difluoromethyl)-1H-pyrazole;

4-(4-methylphenyl)-5-[4-(methylsulfonyl)phenyl]-1-phenyl-3-(difluoromethyl)-1H-pyrazole;

4-(4-ethylphenyl)-5-[4-(methylsulfonyl)phenyl]-1-phenyl-3-(difluoromethyl)-1H-pyrazole;

4-(4-tert-butylphenyl)-5-[4-(methylsulfonyl)phenyl]-1-phenyl-3-(difluoromethyl)-1H-pyrazole;

4-(4-methylthiophenyl)-5-[4-(methylsulfonyl)phenyl]-1-phenyl-3-(difluoromethyl)-1H-pyrazole;

4-(4-methylsulfinylphenyl)-5-[4-(methylsulfonyl)phenyl]-1-phenyl-3-(difluoromethyl)-1H-pyrazole;

4,5-[4-(methylsulfonyl)phenyl]-1-phenyl-3-(difluoromethyl)-1H-pyrazole;

4-(4-hydroxyphenyl)-5-[4-(methylsulfonyl)phenyl]-1-phenyl-3-(difluoromethyl)-1H-pyrazole;

4-(4-methoxyphenyl)-5-[4-(methylsulfonyl)phenyl]-1-phenyl-3-(difluoromethyl)-1H-pyrazole;

4-(4-nitrophenyl)-5-[4-(methylsulfonyl)phenyl]-1-phenyl-3-(difluoromethyl)-1H-pyrazole;

4-(4-aminophenyl)-5-[4-(methylsulfonyl)phenyl]-1-phenyl-3-(difluoromethyl)-1H-pyrazole;

4-(4-N-methylaminophenyl)-5-[4-(methylsulfonyl)phenyl]-1-phenyl-3-(difluoromethyl)-1H-pyrazole;

4-(4-N,N-dimethylaminophenyl)-5-[4-(methylsulfonyl)phenyl]-1-phenyl-3-(difluoromethyl)-1H-pyrazole;

4-(4-acetamidophenyl)-5-[4-(methylsulfonyl)phenyl]-1-phenyl-3-(difluoromethyl)-1H-pyrazole;

4-(4-[N-acetylamino]methylphenyl)-5-[4-(methylsulfonyl)phenyl]-1-phenyl-3-(difluoromethyl)-1H-pyrazole;

1-(4-methylphenyl)-5-[4-(methylsulfonyl)phenyl]-4-phenyl-3-(difluoromethyl)-1H-pyrazole;

1-(4-ethylphenyl)-5-[4-(methylsulfonyl)phenyl]-4-phenyl-3-(difluoromethyl)-1H-pyrazole;

1-(4-tert-butylphenyl)-5-[4-(methyl sulfonyl)phenyl]-4-phenyl-3-(difluoromethyl)-1H-pyrazole;

1-(4-methylthiophenyl)-5-[4-(methylsulfonyl)phenyl]-4-phenyl-3-(difluoromethyl)-1H-pyrazole;

1-(4-methylsulfinylphenyl)-5-[4-methylsulfonyl)phenyl]-4-phenyl-3-(difluoromethyl)-1H-pyrazole;

1,5-[4-(methylsulfonyl)phenyl]-4-phenyl-3-(difluoromethyl)-1H-pyrazole;

1-(4-hydroxyphenyl)-5-[4-(methylsulfonyl)phenyl]-4-phenyl-3-(difluoromethyl)-1H-pyrazole;

1-(4-methoxyphenyl)-5-[4-(methylsulfonyl)phenyl]-4-phenyl-3-(difluoromethyl)-1H-pyrazole;

1-(4-nitrophenyl)-5-[4-(methylsulfonyl)phenyl]-4-phenyl-3-(difluoromethyl)-1H-pyrazole;

1-(4-aminophenyl)-5-[4-(methylsulfonyl)phenyl]-4-phenyl-3-(difluoromethyl)-1H-pyrazole;

1-(4-N-methylaminophenyl)-5-[4-(methylsulfonyl)phenyl]-4-phenyl-3-(difluoromethyl)-1H-pyrazole;

1-(4-N,N-dime[hylaminophenyl)-5-[4-(methylsulfonyl)phenyl]-4-phenyl-3-(difluoromethyl)-1H-pyrazole;

1-(4-acetamidophenyl)-5-[4-(methylsulfonyl)phenyl]-4-phenyl-3-(difluoromethyl)-1H-pyrazole;

1-(4-[N-acetylamino]methylphenyl)-5-[4-(methylsulfonyl)phenyl]-4-phenyl-3-(difluoromethyl)-1H-pyrazole;

4-(4-fluorophenyl)-5-[4-(methylsulfonyl)phenyl]-1-phenyl-1H-pyrazole;

4-(4-chlorophenyl)-5-[4-(methylsulfonyl)phenyl]-1-phenyl-1H-pyrazole;

4-(4-bromophenyl)-5-[4-(methylsulfonyl)phenyl]-1-phenyl-1H-pyrazole;

1,4-bis 4-fluorophenyl)-5-[4-(methylsulfonyl)phenyl]-3-(trifluoromethyl)-1H-pyrazole;

1,4-bis 4-chlorophenyl)-5-[4-(methylsulfonyl)phenyl]-3-(trifluoromethyl)-1H-pyrazole;

1,4-bis 4-bromophenyl)-5-[4-(methylsulfonyl)phenyl]-3-(trifluoromethyl)-1H-pyrazole;

1,4-bis 4-iodophenyl)-5-[4-(methylsulfonyl)phenyl]-3-(trifluoromethyl)-1H-pyrazole;

1,4-bis 2-fluorophenyl)-5-[4-(methylsulfonyl)phenyl]-3-(trifluoromethyl)-1H-pyrazole;

1,4-bis 2-chlorophenyl)-5-[4-(methylsulfonyl)phenyl]-3-(trifluoromethyl)-1H-pyrazole;

1,4-bis 2,4-difluorophenyl)-5-[4-(methylsulfonyl)phenyl]-3-(trifluoromethyl)-1H-pyrazole;

1,4-bis 2,4-dichlorophenyl)-5-[4-(methylsulfonyl)phenyl]-3-(trifluoromethyl)-1H-pyrazole;

5-[4-(methylsulfonyl)phenyl]-1,4-diphenyl-3-trifluoromethyl)-1H-pyrazole;

1,4-bis(4-methylphenyl)-5-[4-(methylsulfonyl)phenyl]-3-(trifluoromethyl)-1H-pyrazole;

1,4-bis(4-ethylphenyl)-5-[4-(methylsulfonyl)phenyl]-3-(trifluoromethyl)-1H-pyrazole;

1,4-bis(4-tert-butylphenyl)-5-[4-(methylsulfonyl)phenyl]-3-(trifluoromethyl)-1H-pyrazole;

1,4-bis(4-methylthiophenyl)-5-[4-(methylsulfonyl)phenyl]-3-(trifluoromethyl)-1H-pyrazole;

1,4-bis(4-methylsulfinylphenyl)-5-[4-(methylsulfonyl)phenyl]-3-(trifluoromethyl)-1H-pyrazole;

1,4,5-tris[4-(methylsulfonyl)phenyl]-3-trifluoromethyl)-1H-pyrazole;

1,4-bis(4-hydroxyphenyl)-5-[4-(methylsulfonyl)phenyl]-3-(trifluoromethyl)-1H-pyrazole;

1,4-bis(4-methoxyphenyl)-5-[4-(methylsulfonyl)phenyl]-3-(trifluoromethyl)-1H-pyrazole;

1,4-bis(4-nitrophenyl)-5-[4-(methylsulfonyl)phenyl]-3-(trifluoromethyl)-1H-pyrazole;

1,4-bis(4-aminophenyl)-5-[4-(methylsulfonyl)phenyl]-3-(trifluoromethyl)-1H-pyrazole;

1,4-bis(4-N-methylaminophenyl)-5-[4-(methylsulfonyl)phenyl]-3-(trifluoromethyl)-1H-pyrazole;

1,4-bis4-N,N-dimethylaminophenyl)-5-[4-(methylsulfonyl)phenyl]-3-(trifluoromethyl)-1H-pyrazole;

1,4-bis(4-trifluoromethylphenyl)-5-[4-(methylsulfonyl)phenyl]-3-(trifluoromethyl)-1H-pyrazole;

1,4-bis(4-acetamidophenyl)-5-[4-(methylsulfonyl)phenyl]-3-(trifluoromethyl)-1H-pyrazole;

1,4-bis(4-[N-acetylamino]methylphenyl)-5-[4-(methylsulfonyl)phenyl]-3-(trifluoromethyl)-1H-pyrazole;

1,4-bis(4-fluorophenyl)-5-[4-(methylsulfonyl)phenyl]-3-(difluoromethyl)-1H-pyrazole;

1,4-bis(4-fluorophenyl)-5-[4-(methylsulfonyl)phenyl]-3-chlorodifluoromethyl-1H-pyrazole;

1,4-bis(4-fluorophenyl)-5-[4-(methylsulfonyl)phenyl]-3-pentafluoroethyl-1H-pyrazole;

1,4-bis(4-fluorophenyl)-5-[4-(methylsulfonyl)phenyl]-3-heptafluoropropyl-1H-pyrazole;

1,4-bis(4-chlorophenyl)-5-[4-(methylsulfonyl)phenyl]-3-(difluoromethyl)-1H-pyrazole;

1,4-bis(4-bromophenyl)-5-[4-(methylsulfonyl)phenyl]-3-(difluoromethyl)-1H-pyrazole;

1,4-bis(4-iodophenyl)-5-[4-(methylsulfonyl)phenyl]-3-(difluoromethyl)-1H-pyrazole;

1,4-bis(2-fluorophenyl)-5-[4-(methylsulfonyl)phenyl]-3-(difluoromethyl)-1H-pyrazole;

1,4-bis(2-chlorophenyl)-5-[4-(methylsulfonyl)phenyl]-3-(difluoromethyl)-1H-pyrazole;

4-(2,4-difluorophenyl)-5-[4-(methylsulfonyl)phenyl]-1-phenyl-3-(difluoromethyl)-1H-pyrazole;

4-(2,4-dichlorophenyl)-5-[4-(methylsulfonyl)phenyl]-1-phenyl-3-(difluoromethyl)-1H-pyrazole;

5-[4-(methylsulfonyl)phenyl]-1,4-diphenyl-3-(difluoromethyl)-1H-pyrazole;

1,4-bis(4-methylphenyl)-5-[4-(methylsulfonyl)phenyl]-3-(difluoromethyl)-1H-pyrazole;

1,4-bis(4-ethylphenyl)-5-[4-(methylsulfonyl)phenyl]-3-(difluoromethyl)-1H-pyrazole;

1,4-bis(4-tert-butylphenyl)-5-[4-(methylsulfonyl)phenyl]-3-(difluoromethyl)-1H-pyrazole;

1,4-bis(4-methylthiophenyl)-5-[4-(methylsulfonyl)phenyl]-3-(difluoromethyl)-1H-pyrazole;

1,4-bis(4-methylsulfinylphenyl)-5-[4-(methylsulfonyl)phenyl-3-(difluoromethyl)-1H-pyrazole;

1,4,5-tris[4-(methylsulfonyl)phenyl]-3-(difluoromethyl)-1H-pyrazole;

1,4-bis(4-hydroxyphenyl)-5-[4-(methylsulfonyl)phenyl]-3-(difluoromethyl)-1H-pyrazole;

1,4-bis(4-methoxyphenyl)-5-[4-(methylsulfonyl)phenyl]-3-(difluoromethyl)-1H-pyrazole;

1,4-bis(4-nitrophenyl)-5-[4-(methylsulfonyl)phenyl]-3-(difluoromethyl)-1H-pyrazole;

1,4-bis(4-aminophenyl)-5-[4-(methylsulfonyl)phenyl]-3-(difluoromethyl)-1H-pyrazole;

1,4-bis(4-N-methylaminophenyl)-5-[4-(methylsulfonyl)phenyl]-3-(difluoromethyl)-1H-pyrazole;

1,4-bis(4-N,N-dimethylaminophenyl)-5-[4-(methylsulfonyl)phenyl]-3-(difluoromethyl)-1H-pyrazole;

1,4-bis(4-difluoromethylphenyl)-5-[4-(methylsulfonyl)phenyl]-3-(difluoromethyl)-1H-pyrazole;

1,4-bis(4-acetamidophenyl)-5-[4-(methylsulfonyl)phenyl]-3-(difluoromethyl)-1H-pyrazole;

1,4-bis(4-[N-acetylamino]methylphenyl)-5-[4-(methylsulfonyl)phenyl]-3-(difluoromethyl)-1H-pyrazole;

1,4-bis(4-fluorophenyl)-5-[4-(methylsulfonyl)phenyl]-1H-pyrazole;

1,4-bis(4-chlorophenyl)-5-[4-(methylsulfonyl)phenyl]-1H-pyrazole;

1,4-bis(4-bromophenyl)-5-[4-(methylsulfonyl)phenyl]-1H-pyrazole;

4-(4-fluorophenyl)-5-[4-(methylsulfonyl)phenyl]-1-phenyl-3-(methyl)-1H-pyrazole;

4-(4-fluorophenyl)-5-[4-(methylsulfonyl)phenyl]-1-phenyl-3-(ethyl)-1H-pyrazole;

4-(4-fluorophenyl)-5-[4-(methylsulfonyl)phenyl]-1-phenyl-3-(propyl)-1H-pyrazole;

4-(4-fluorophenyl)-5-[4-(methylsulfonyl)phenyl]-1-phenyl-3-(cyano)-1H-pyrazole;

4-[4-(4-fluorophenyl)-1-phenyl-3-(trifluoromethyl)-1H-pyrazol-5-yl]benzenesulfonamide;

4-[4-(4-chlorophenyl)-1-phenyl-3-(trifluoromethyl)-1H-pyrazol-5-yl]benzenesulfonamide;

4-[4-(4-bromophenyl)-1-phenyl-3-(trifluoromethyl)-1H-pyrazol-5-yl]benzenesulfonamide;

4-[4-(4-iodophenyl)-1-phenyl-3-(trifluoromethyl)-1H-pyrazol-5-yl]benzenesulfonamide;

4-[4-(2-fluorophenyl)-1-phenyl-3-(trifluoromethyl)-1H-pyrazol-5-yl]benzenesulfonamide;

4-[4-(2-chlorophenyl)-1-phenyl-3-(trifluoromethyl)-1H-pyrazol-5-yl]benzenesulfonamide;

4-[4-(2,4-difluorophenyl)-1-phenyl-3-(trifluoromethyl)-1H-pyrazol-5-yl]benzenesulfonamide;

4-[4-(2,4-dichlorophenyl)-1-phenyl-3-(trifluoromethyl)-1H-pyrazol-5-yl]benzenesulfonamide;

4-[1,4-diphenyl-3-(trifluoromethyl)-1H-pyrazol-5-yl]benzenesulfonamide;

4-[4-(4-methylphenyl)-1-phenyl-3-(trifluoromethyl)-1H-pyrazol 1-5-yl]benzenesulfonamide;

4-[4-(4-ethylphenyl)-1-phenyl-3-(trifluoromethyl)-1H-pyrazol-5-yl]benzenesulfonamide;

4-[4-(4-tert-butylphenyl)-1-phenyl-3-(trifluoromethyl)-1H-pyrazol-5-yl]benzenesulfonamide;

4-[4-(4-methylthiophenyl)-1-phenyl-3-(trifluoromethyl)-1H-pyrazol-5-yl]benzenesulfonamide;

4-[4-(4-methylsulfinylphenyl)-1-phenyl-3-(trifluoromethyl)-1H-pyrazol -5-yl]benzenesulfonamide;

4-[4,1-phenyl-3-(trifluoromethyl)-1H-pyrazol-5-yl]benzenesulfonamide;

4-[4-(4-hydroxyphenyl)-1-phenyl-3-(trifluoromethyl)-1H-pyrazol-5-yl]benzenesulfonamide;

4-[4-(4-methoxyphenyl)-1-phenyl-3-(trifluoromethyl)-1H-pyrazol-5-yl]benzenesulfonamide;

4-[4-(4-nitrophenyl)-1-phenyl-3-(trifluoromethyl)-1H-pyrazol-5-yl]benzenesulfonamide;

4-[4-4-aminophenyl)-1-phenyl-3-(trifluoromethyl)-1H-pyrazol-5-yl]benzenesulfonamide;

4-[4-4-N-methylaminophenyl)-1-phenyl-3-(trifluoromethyl)-1H-pyrazol-5-yl]benzenesulfonamide;

4-[4-4-N,N-dimethylaminophenyl)-1-phenyl-3-(trifluoromethyl)-1H-pyrazol-5-yl]benzenesulfonamide;

4-[4-4-trifluoromethylphenyl)-1-phenyl-3-(trifluoromethyl)-1H-pyrazol-5-yl]benzenesulfonamide;

4-[4-4-acetamidophenyl)-1-phenyl-3-(trifluoromethyl)-1H-pyrazol-5-yl]benzenesulfonamide;

4-[4-4-[N-acetylamino]methylphenyl)-1-phenyl-3-(trifluoromethyl)-1H-pyrazol-5-yl]benzenesulfonamide;

4-[1-(4-fluorophenyl)-4-phenyl-3-(trifluoromethyl)-1H-pyrazol-5-yl]benzenesulfonamide;

4-[1-(4-chlorophenyl)-4-phenyl-3-(trifluoromethyl)-1H-pyrazol-5-yl]benzenesulfonamide;

4-[1-(4-bromophenyl)-4-phenyl-3-(trifluoromethyl)-1H-pyrazol-5-yl]benzenesulfonamide;

4-[1-(4-iodophenyl)-4-phenyl-3-(trifluoromethyl)-1H-pyrazol-5-yl]benzenesulfonamide;

4-[1-(4-methylphenyl)-4-phenyl-3-(trifluoromethyl)-1H-pyrazol-5-yl]benzenesulfonamide;

4-[1-(4-ethylphenyl)-4-phenyl-3-(trifluoromethyl)-1H-pyrazol-5-yl]benzenesulfonamide;

4-[1-(4-tert-butylphenyl)-4-phenyl-3-(trifluoromethyl)-1H-pyrazol-5-yl]benzenesulfonamide;

4-[1-(4-methylthiophenyl)-4-phenyl-3-(trifluoromethyl)-1H-pyrazol-5-yl]benzenesulfonamide;

4-[1-(4-methylsulfinylphenyl)-4-phenyl-3-(trifluoromethyl)-1H-pyrazol-5-yl]benzene sulfonamide;

4-[1,4-phenyl-3-(trifluoromethyl)-1H-pyrazol-5-yl]benzenesulfonamide;

4-[1-(4-hydroxyphenyl)-4-phenyl-3-(trifluoromethyl)-1H-pyrazol-5-yl]benzenesulfonamide;

4-[1-(4-methoxyphenyl)-4-phenyl-3-(trifluoromethyl)-1H-pyrazol-5-yl]benzenesulfonamide;

4-[1-(4-nitrophenyl)-4-phenyl-3-(trifluoromethyl)-1H-pyrazol-5-yl]benzenesulfonamide;

4-[1-(4-aminophenyl)-4-phenyl-3-(trifluoromethyl)-1H-pyrazol-5-yl]benzenesulfonamide;

4-[1-(4-N-methylaminophenyl)-4-phenyl-3-(trifluoromethyl)-1H-pyrazol-5-yl]benzenesulfonamide;

4-[1-(4-N,N-dimethylaminophenyl)-4-phenyl-3-(trifluoromethyl)-1H-pyrazol-5-yl]benzenesulfonamide;

4-[1-(4-trifluoromethylphenyl)-4-phenyl-3-(trifluoromethyl)-1H-pyrazol-5-yl]benzenesulfonamide;

4-[1-(4-acetamidophenyl)-4-phenyl-3-(trifluoromethyl)-1H-pyrazol-5-yl]benzenesulfonamide;

4-[1-(4-[N-acetylamino]methylphenyl)-4-phenyl-3-(trifluoromethyl)-1H-pyrazol-5-yl]benzenesulfonamide;

4-[4-4-fluorophenyl)-1-phenyl-3-(difluoromethyl)-1H-pyrazol-5-yl]benzenesulfonamide;

4-[4-4-fluorophenyl)-1-phenyl-3-chlorodifluoromethyl-1H-pyrazol-5-yl]benzenesulfonamide;

4-[4-4-fluorophenyl)-1-phenyl-3-pentafluoroethyl-1H-pyrazol-5-yl]benzenesulfonamide;

4-[4-4-fluorophenyl)-1-phenyl-3-heptafluoropropyl-1H-pyrazol-5-yl]benzenesulfonamide;

4-[4-4-chlorophenyl)-1-phenyl-3-(difluoromethyl)-1H-pyrazol-5-yl]benzenesulfonamide;

4-[4-4-bromophenyl)-1-phenyl-3-(difluoromethyl)-1H-pyrazol-5-yl]benzenesulfonamide;

4-[4-4-iodophenyl)-1-phenyl-3-(difluoromethyl)-1H-pyrazol-5-yl]benzenesulfonamide;

4-[4-2-fluorophenyl)-1-phenyl-3-(difluoromethyl)-1H-pyrazol-5-yl]benzenesulfonamide;

4-[4-2-chlorophenyl)-1-phenyl-3-(difluoromethyl)-1H-pyrazol-5-yl]benzenesulfonamide;

4-[4-2,4-difluorophenyl)-1-phenyl-3-(difluoromethyl)-1H-pyrazol-5-yl]benzenesulfonamide;

4-[4-2,4-dichlorophenyl)-1-phenyl-3-(difluoromethyl)-1H-pyrazol-5-yl]benzenesulfonamide;

4-[1,4-diphenyl-3-(difluoromethyl)-1H-pyrazol-5-yl]benzenesulfonamide;

4-[4-(4-methylphenyl)-1-phenyl-3-(difluoromethyl)-1H-pyrazol-5-yl]benzenesulfonamide;

4-[4-(4-ethylphenyl)-1-phenyl-3-(difluoromethyl)-1H-pyrazol-5-yl]benzenesulfonamide;

4-[4-(4-tert-butylphenyl)-1-phenyl-3-(difluoromethyl)-1H-pyrazol-5-yl]benzenesulfonamide;

4-[4-(4-methylthiophenyl)-1-phenyl-3-(difluoromethyl)-1H-pyrazol-5-yl]benzenesulfonamide;

4-[4-(4-methylsulfinylphenyl)-1-phenyl-3-(difluoromethyl)-1H-pyrazol-5-yl]benzenesulfonamide;

4-[4,1-phenyl-3-(difluoromethyl)-1H-pyrazol-5-yl]benzenesulfonamide;

4-[4-(4-hydroxyphenyl)-1-phenyl-3-(difluoromethyl)-1H-pyrazol-5-yl]benzenesulfonamide;

4-[4-4-methoxyphenyl)-1-phenyl-3-(difluoromethyl)-1H-pyrazol-5-yl]benzenesulfonamide;

4-[4-4-nitrophenyl)-1-phenyl-3-(difluoromethyl)-1H-pyrazol-5-yl]benzenesulfonamide;

4-[4-4-aminophenyl)-1-phenyl-3-(difluoromethyl)-1H-pyrazol-5-yl]benzenesulfonamide;

4-[4-4-N-methylaminophenyl)-1-phenyl-3-(difluoromethyl)-1H-pyrazol-5-yl]benzenesulfonamide;

4-[4-4-N,N-dimethylaminophenyl)-1-phenyl-3-(difluoromethyl)-1H-pyrazol-5-yl]benzenesulfonamide;

4-[4-4-acetamidophenyl)-1-phenyl-3-(difluoromethyl)-1H-pyrazol-5-yl]benzenesulfonamide;

4-[4-4-[N-acetylamino]methylphenyl)-1-phenyl-3-(difluoromethyl)-1H-pyrazol-5-yl]benzenesulfonamide;

4-[1-4-methylphenyl)-4-phenyl-3-(difluoromethyl)-1H-pyrazol-5-yl]benzenesulfonamide;

4-[1-4-ethylphenyl)-4-phenyl-3-(difluoromethyl)-1H-pyrazol-5-yl]benzenesulfonamide;

4-[1-4-tert-butylphenyl)-4-phenyl-3-(difluoromethyl)-1H-pyrazol-5-yl]benzenesulfonamide;

4-[1-4-methylthiophenyl)-4-phenyl-3-(difluoromethyl)-1H-pyrazol-5-yl]benzenesulfonamide;

4-[1-4-methylsulfinylphenyl)-4-phenyl-3-(difluoromethyl)-1H-pyrazol-5-yl]benzenesulfonamide;
4-[1,4-phenyl-3-(difluoromethyl)-1H-pyrazol-5-yl]benzenesulfonamide;
4-[1-(4-hydroxyphenyl)-4-phenyl-3-(difluoromethyl)-1H-pyrazol-5-yl]benzenesulfonamide;
4-[1-(4-methoxyphenyl)-4-phenyl-3-(difluoromethyl)-1H-pyrazol-5-yl]benzenesulfonamide;
4-[1-(4-nitrophenyl)-4-phenyl-3-(difluoromethyl)-1H-pyrazol-5-yl]benzenesulfonamide;
4-[1-(4-aminophenyl)-4-phenyl-3-(difluoromethyl)-1H-pyrazol-5-yl]benzenesulfonamide;
4-[1-(4-N-methylaminophenyl)-4-phenyl-3-(difluoromethyl)-1H-pyrazol-5-yl]benzenesulfonamide;
4-[1-(4-N,N-dimethylaminophenyl)-4-phenyl-3-(difluoromethyl)-1H-pyrazol-5-yl]benzenesulfonamide;
4-[1-(4-acetamidophenyl)-4-phenyl-3-(difluoromethyl)-1H-pyrazol-5-yl]benzenesulfonamide;
4-[1-(4-[N-acetylamino]methylphenyl)-4-phenyl-3-(difluoromethyl)-1H-pyrazol-5-yl]benzenesulfonamide;
4-[4-(4-fluorophenyl)-1-phenyl-1H-pyrazol-5-yl]benzenesulfonamide;
4-[4-(4-chlorophenyl)-1-phenyl-1H-pyrazol-5-yl]benzenesulfonamide;
4-[4-(4-bromophenyl)-1-phenyl-1H-pyrazol-5-yl]benzenesulfonamide;
4-[1,4-bis(4-fluorophenyl)-3-(trifluoromethyl)-1H-pyrazol-5-yl]benzenesulfonamide;
4-[1,4-bis(4-chlorophenyl)-3-(trifluoromethyl)-1H-pyrazol-5-yl]benzenesulfonamide;
4-[1,4-bis(4-bromophenyl)-3-(trifluoromethyl)-1H-pyrazol-5-yl]benzenesulfonamide;
4-[1,4-bis(4-iodophenyl)-3-(trifluoromethyl)-1H-pyrazol-5-yl]benzenesulfonamide;
4-[1,4-bis(2-fluorophenyl)-3-(trifluoromethyl)-1H-pyrazol-5-yl]benzenesulfonamide;
4-[1,4-bis(2-chlorophenyl)-3-(trifluoromethyl)-1H-pyrazol-5-yl]benzenesulfonamide;
4-[1,4-bis(2,4-difluorophenyl)-3-(trifluoromethyl)-1H-pyrazol-5-yl]benzenesulfonamide;
4-[1,4-bis(2,4-dichlorophenyl)-3-(trifluoromethyl)-1H-pyrazol-5-yl]benzenesulfonamide;
4-[1,4-diphenyl-3-(trifluoromethyl)-1H-pyrazol-5-yl]benzenesulfonamide;
4-[1,4-bis(4-methylphenyl)-3-(trifluoromethyl)-1H-pyrazol-5-yl]benzenesulfonamide;
4-[1,4-bis(4-ethylphenyl)-3-(trifluoromethyl)-1H-pyrazol-5-yl]benzenesulfonamide;
4-[1,4-bis(4-tert-butylphenyl)-3-(trifluoromethyl)-1H-pyrazol-5-yl]benzenesulfonamide;
4-[1,4-bis(4-methylthiophenyl)-3-(trifluoromethyl)-1H-pyrazol-5-yl]benzenesulfonamide;
4-[1,4-bis(4-methylsulfinylphenyl)-3-(trifluoromethyl)-1H-pyrazol-5-yl]benzenesulfonamide;
4-[1,4,5-tris[4-(methylsulfonyl)phenyl]-3-(trifluoromethyl)-1H-pyrazol-5-yl]benzenesulfonamide;
4-[1,4-bis(4-hydroxyphenyl)-3-(trifluoromethyl)-1H-pyrazol-5-yl]benzenesulfonamide;
4-[1,4-bis(4-methoxyphenyl)-3-(trifluoromethyl)-1H-pyrazol-5-yl]benzenesulfonamide;
4-[1,4-bis(4-nitrophenyl)-3-(trifluoromethyl)-1H-pyrazol-5-yl]benzenesulfonamide;
4-[1,4-bis(4-aminophenyl)-3-(trifluoromethyl)-1H-pyrazol-5-yl]benzenesulfonamide;
4-[1,4-bis(4-N-methylaminophenyl)-3-(trifluoromethyl)-1H-pyrazol-5-yl]benzenesulfonamide;
4-[1,4-bis(4-N,N-dimethylaminophenyl)-3-(trifluoromethyl)-1H-pyrazol-5-yl]benzenesulfonamide;
4-[1,4-bis(4-trifluoromethylphenyl)-3-(trifluoromethyl)-1H-pyrazol-5-yl]benzenesulfonamide;
4-[1,4-bis(4-acetamidophenyl)-3-(trifluoromethyl)-1H-pyrazol-5-yl]benzenesulfonamide;
4-[1,4-bis(4-[N-acetylamino]methylphenyl)-3-(trifluoromethyl)-1H-pyrazol-5-yl]benzenesulfonamide;
4-[1,4-bis(4-fluorophenyl)-3-(difluoromethyl)-1H-pyrazol-5-yl]benzenesulfonamide;
4-[1,4-bis(4-fluorophenyl)-3-chlorodifluoromethyl-1H-pyrazol-5-yl]benzenesulfonamide;
4-[1,4-bis(4-fluorophenyl)-3-pentafluoroethyl-1H-pyrazol-5-yl]benzenesulfonamide;
4-[1,4-bis(4-fluorophenyl)-3-heptafluoropropyl-1H-pyrazol-5-yl]benzenesulfonamide;
4-[1,4-bis(4-chlorophenyl)-3-(difluoromethyl)-1H-pyrazol-5-yl]benzenesulfonamide;
4-[1,4-bis(4-bromophenyl)-3-(difluoromethyl)-1H-pyrazol-5-yl]benzenesulfonamide;
4-[1,4-bis(4-iodophenyl)-3-(difluoromethyl)-1H-pyrazol-5-yl]benzenesulfonamide;
4-[1,4-bis(2-fluorophenyl)-3-(difluoromethyl)-1H-pyrazol-5-yl]benzenesulfonamide;
4-[1,4-bis(2-chlorophenyl)-3-(difluoromethyl)-1H-pyrazol-5-yl]benzenesulfonamide;
4-[4-(2,4-difluorophenyl)-1-phenyl-3-(difluoromethyl)-1H-pyrazol-5-yl]benzenesulfonamide;
4-[4-(2,4-dichlorophenyl)-1-phenyl-3-(difluoromethyl)-1H-pyrazol-5-yl]benzenesulfonamide;
4-[1,4-diphenyl-3-(difluoromethyl)-1H-pyrazol-5-yl]benzenesulfonamide;
4-[1,4-bis(4-methylphenyl)-3-(difluoromethyl)-1H-pyrazol-5-yl]benzenesulfonamide;
4-[1,4-bis(4-ethylphenyl)-3-(difluoromethyl)-1H-pyrazol-5-yl]benzenesulfonamide;
4-[1,4-bis(4-tert-butylphenyl)-3-(difluoromethyl)-1H-pyrazol-5-yl]benzenesulfonamide;
4-[1,4-bis(4-methylthiophenyl)-3-(difluoromethyl)-1H-pyrazol-5-yl]benzenesulfonamide;
4-[1,4-bis(4-methylsulfinylphenyl)-5-[4-(methylsulfonyl)phenyl-3-(difluoromethyl)-1H-pyrazol-5-yl]benzenesulfonamide;
4-[1,4,5-tris[4-(methylsulfonyl)phenyl]-3-(difluoromethyl)-1H-pyrazol-5-yl]benzenesulfonamide;
4-[1,4-bis(4-hydroxyphenyl)-3-(difluoromethyl)-1H-pyrazol-5-yl]benzenesulfonamide;
4-[1,4-bis(4-methoxyphenyl)-3-(difluoromethyl)-1H-pyrazol-5-yl]benzenesulfonamide;
4-[1,4-bis(4-nitrophenyl)-3-(difluoromethyl)-1H-pyrazol-5-yl]benzenesulfonamide;

4-[1,4-bis(4-aminophenyl)-3-(difluoromethyl)-1H-pyrazol-5-yl]benzenesulfonamide;

4-[1,4-bis(4-N-methylaminophenyl)-3-(difluoromethyl)-1H-pyrazol-5-yl]benzenesulfonamide;

4-[1,4-bis(4-N,N-dimethylaminophenyl)-3-(difluoromethyl)-1H-pyrazol-5-yl]benzenesulfonamide;

4-[1,4-bis(4-difluoromethylphenyl)-3-(difluoromethyl)-1H-pyrazol-5-yl]benzenesulfonamide;

4-[1,4-bis(4-acetamidophenyl)-3-(difluoromethyl)-1H-pyrazol-5-yl]benzenesulfonamide;

4-[1,4-bis(4-[N-acetylamino]methylphenyl)-3-(difluoromethyl)-1H-pyrazol-5-yl]benzenesulfonamide;

4-[1,4-bis(4-fluorophenyl)-1H-pyrazol-5-yl]benzenesulfonamide;

4-[1,4-bis(4-chlorophenyl)-1H-pyrazol-5-yl]benzenesulfonamide;

4-[1,4-bis(4-bromophenyl)-1H-pyrazol-5-yl]benzenesulfonamide;

4-[4-(4-fluorophenyl)-1-phenyl-3-(methyl)-1H-pyrazol-5-yl]benzenesulfonamide;

4-[4-(4-fluorophenyl)-1-phenyl-3-(ethyl)-1H-pyrazol-5-yl]benzenesulfonamide;

4-[4-(4-fluorophenyl)-1-phenyl-3-(propyl)-1H-pyrazol-5-yl]benzenesulfonamide; and 4-[4-(4-fluorophenyl)-1-phenyl-3-(cyano)-1H-pyrazol-5-yl]benzenesulfonamide.

Within Formula I there is a subclass of compounds of high interest represented by Formula II:

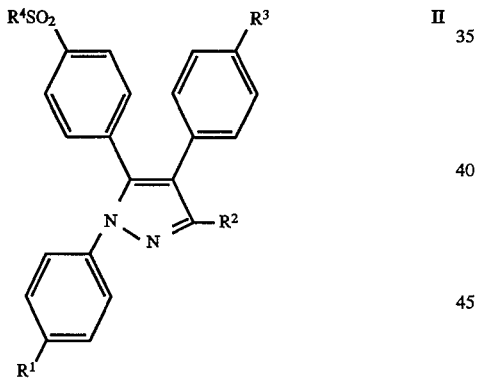

wherein $R^1$ is selected from the group hydrido, halo, alkyl, alkylthio, alkylsulfinyl, alkylsulfonyl, nitro, amino, N-monoalkylamino, N,N-dialkylamino, acylamino, acylaminoalkyl, haloalkyl, hydroxy and alkoxy; wherein $R^2$ is selected from hydrido, alkyl, cyano and haloalkyl; wherein $R^3$ is selected from the group hydrido, halo, alkyl, alkylthio, alkylsulfinyl, alkylsulfonyl, nitro, amino, N-monoalkylamino, N,N-dialkylamino, acylamino, acylaminoalkyl, haloalkyl, hydroxy and alkoxy; and wherein $R^4$ is alkyl or amino; or a pharmaceutically-acceptable salt thereof.

A preferred class of compounds consists of those compounds of Formula II wherein $R^1$ is selected from the group hydrido, halo, lower alkyl, lower alkylthio, lower alkylsulfinyl, lower alkylsulfonyl, nitro, amino, N-monoalkylamino, N,N-dialkylamino, acylamino, acylaminoalkyl, lower haloalkyl, hydroxy and lower alkoxy; wherein $R^2$ is selected from hydrido, lower alkyl, cyano and lower haloalkyl; wherein $R^3$ is selected from the group hydrido, halo, lower alkyl, lower alkylthio, lower alkylsulfinyl, lower alkylsulfonyl, nitro, amino, N-monoalkylamino, N,N-dialkylamino, acylamino, acylaminoalkyl, lower haloalkyl, hydroxy and lower alkoxy; and wherein $R^4$ is lower alkyl or amino; or a pharmaceutically-acceptable salt thereof.

A class of compounds of particular interest consists of those compounds of Formula II wherein $R^1$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; wherein $R^2$ is selected from hydrido, cyano, methyl, ethyl, propyl, trifluoromethyl, difluorochloromethyl, difluoromethyl, pentafluoroethyl and heptafluoropropyl; wherein $R^3$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; and wherein $R^4$ is methyl or amino; or a pharmaceutically-acceptable salt thereof.

A family of specific compounds of particular interest within Formula II consists of compounds and pharmaceutically-acceptable salts thereof as follows:

4-(4-fluorophenyl)-5-[4-(methylsulfonyl)phenyl]-1-phenyl-3-(trifluoromethyl)-1H-pyrazole;

4-(4-chlorophenyl)-5-[4-(methylsulfonyl)phenyl]-1-phenyl-3-(trifluoromethyl)-1H-pyrazole;

4-(4-bromophenyl)-5-[4-(methylsulfonyl)phenyl]-1-phenyl-3-(trifluoromethyl)-1H-pyrazole;

4-(4-iodophenyl)-5-[4-(methylsulfonyl)phenyl]-1-phenyl-3-(trifluoromethyl)-1H-pyrazole;

5-[4-(methylsulfonyl)phenyl]-1,4-diphenyl-3-(trifluoromethyl)-1H-pyrazole;

4-(4-methylphenyl)-5-[4-(methylsulfonyl)phenyl]-1-phenyl-3-(trifluoromethyl)-1H-pyrazole;

4-(4-methylthiophenyl)-5-[4-(methylsulfonyl)phenyl]-1-phenyl-3-(trifluoromethyl)-1H-pyrazole;

4-(4-methylsulfinylphenyl)-5-[4-(methylsulfonyl)phenyl]-1-phenyl-3-(trifluoromethyl)-1H-pyrazole;

4-(4-hydroxyphenyl)-5-[4-(methylsulfonyl)phenyl]-1-phenyl-3-(trifluoromethyl)-1H-pyrazole;

4-(4-methoxyphenyl)-5-[4-(methylsulfonyl)phenyl]-1-phenyl-3-(trifluoromethyl)-1H-pyrazole;

4-(4-nitrophenyl)-5-[4-(methylsulfonyl)phenyl]-1-phenyl-3-(trifluoromethyl)-1H-pyrazole;

4-(4-aminophenyl)-5-[4-(methylsulfonyl)phenyl]-1-phenyl-3-(trifluoromethyl)-1H-pyrazole;

4-(4-N-methylaminophenyl)-5-[4-(methylsulfonyl)phenyl]-1-phenyl-3-(trifluoromethyl)-1H-pyrazole;

4-(4-N,N-dimethylaminophenyl)-5-[4-(methylsulfonyl)phenyl]-1-phenyl-3-(trifluoromethyl)-1H-pyrazole;

4-(4-trifluoromethylphenyl)-5-[4-(methylsulfonyl)phenyl]-1-phenyl-3-(trifluoromethyl)-1H-pyrazole;

4-(4-acetamidophenyl)-5-[4-(methylsulfonyl)phenyl]-1-phenyl-3-(trifluoromethyl)-1H-pyrazole;

4-(4-[N-acetylamino]methylphenyl)-5-[4-(methylsulfonyl)phenyl]-1-phenyl-3-(trifluoromethyl)-1H-pyrazole;

1-(4-fluorophenyl)-5-[4-(methylsulfonyl)phenyl]-4-phenyl-3-(trifluoromethyl)-1H-pyrazole;

1-(4-chlorophenyl)-5-[4-(methylsulfonyl)phenyl]-4-phenyl-3-(trifluoromethyl)-1H-pyrazole;

1-(4-bromophenyl)-5-[4-(methylsulfonyl)phenyl]-4-phenyl-3-(trifluoromethyl)-1H-pyrazole;

1-(4-iodophenyl)-5-[4-(methylsulfonyl)phenyl]-4-phenyl-3-(trifluoromethyl)-1H-pyrazole;

1-(4-methylphenyl)-5-[4-(methylsulfonyl)phenyl]-4-phenyl-3-(trifluoromethyl)-1H-pyrazole;

1-(4-methylthiophenyl)-5-[4-(methylsulfonyl)phenyl]-4-phenyl-3-(trifluoromethyl)-1H-pyrazole;

1-(4-hydroxyphenyl)-5-[4-(methylsulfonyl)phenyl]-4-phenyl-3-(trifluoromethyl)-1H-pyrazole;

1-(4-methoxyphenyl)-5-[4-(methylsulfonyl)phenyl]-4-phenyl-3-(trifluoromethyl)-1H-pyrazole;

1-(4-nitrophenyl)-5-[4-(methylsulfonyl)phenyl]-4-phenyl-3-(trifluoromethyl)-1H-pyrazole;

1-(4-aminophenyl)-5-[4-(methylsulfonyl)phenyl]-4-phenyl-3-(trifluoromethyl)-1H-pyrazole;

1-(4-N-methylaminophenyl)-5-[4-(methylsulfonyl)phenyl]-4-phenyl-3-(trifluoromethyl)-1H-pyrazole;

1-(4-N,N-dimethylaminophenyl)-5-[4-(methylsulfonyl)phenyl]-4-phenyl-3-(trifluoromethyl)-1H-pyrazole;

1-(4-trifluoromethylphenyl)-5-[4-(methylsulfonyl)phenyl]-4-phenyl-3-(trifluoromethyl)-1H-pyrazole;

1-(4-acetamidophenyl)-5-[4-(methylsulfonyl)phenyl]-4-phenyl-3-(trifluoromethyl)-1H-pyrazole;

4-(4-fluorophenyl)-5-[4-(methylsulfonyl)phenyl]-1-phenyl-3-(difluoromethyl)-1H-pyrazole;

4-(4-fluorophenyl)-5-[4-(methylsulfonyl)phenyl]-1-phenyl-1H-pyrazole;

4-(4-fluorophenyl)-5-[4-(methylsulfonyl)phenyl]-1-phenyl-3-(methyl)-1H-pyrazole;

4-(4-fluorophenyl)-5-[4-(methylsulfonyl)phenyl]-1-phenyl-3-(cyano)-1H-pyrazole;

1,4-bis(4-fluorophenyl)-5-[4-(methylsulfonyl)phenyl]-3-(trifluoromethyl)-1H-pyrazole;

5-[4-(methylsulfonyl)phenyl]-1,4-diphenyl-3-(difluoromethyl)-1H-pyrazole;

4-[4-(4-fluorophenyl)-1-phenyl-3-(trifluoromethyl)-1H-pyrazol-5-yl]benzenesulfonamide;

4-[4-(4-chlorophenyl)-1-phenyl-3-(trifluoromethyl)-1H-pyrazol-5-yl]benzenesulfonamide;

4-[4-(4-bromophenyl)-1-phenyl-3-(trifluoromethyl)-1H-pyrazol-5-yl]benzenesulfonamide;

4-[4-(4-iodophenyl)-1-phenyl-3-(trifluoromethyl)-1H-pyrazol-5-yl]benzenesulfonamide;

4-[1,4-diphenyl-3-(trifluoromethyl)-1H-pyrazol-5-yl]benzenesulfonamide;

4-[4-(4-methylphenyl)-1-phenyl-3-(trifluoromethyl)-1H-pyrazol-5-yl]benzenesulfonamide;

4-[4-(4-methylthiophenyl)-1-phenyl-3-(trifluoromethyl)-1H-pyrazol-5-yl]benzenesulfonamide;

4-[4-(4-methylsulfinylphenyl)-1-phenyl-3-(trifluoromethyl)-1H-pyrazol-5-yl]benzenesulfonamide;

4-[4-(4-hydroxyphenyl)-1-phenyl-3-(trifluoromethyl)-1H-pyrazol-5-yl]benzenesulfonamide;

4-[4-(4-methoxyphenyl)-1-phenyl-3-(trifluoromethyl)-1H-pyrazol-5-yl]benzenesulfonamide;

4-[4-4-nitrophenyl)-1-phenyl-3-(trifluoromethyl)-1H-pyrazol-5-yl]benzenesulfonamide;

4-[4-4-aminophenyl)-1-phenyl-3-(trifluoromethyl)-1H-pyrazol-5-yl]benzenesulfonamide;

4-[4-4-N-methylaminophenyl)-1-phenyl-3-(trifluoromethyl)-1H-pyrazol-5-yl]benzenesulfonamide;

4-[4-4-N,N-dimethylaminophenyl)-1-phenyl-3-(trifluoromethyl)-1H-pyrazol-5-yl]benzenesulfonamide;

4-[4-4-trifluoromethylphenyl)-1-phenyl-3-(trifluoromethyl)-1H-pyrazol-5-yl]benzenesulfonamide;

4-[4-(4-acetamidophenyl)-1-phenyl-3-(trifluoromethyl)-1H-pyrazol-5-yl]benzenesulfonamide;

4-[4-(4-[N-acetylamino]methylphenyl)-1-phenyl-3-(trifluoromethyl)-1H-pyrazol-5-yl]benzenesulfonamide;

4-[1-(4-fluorophenyl)-4-phenyl-3-(trifluoromethyl)-1H-pyrazol-5-yl]benzenesulfonamide;

4-[1-(4-chlorophenyl)-4-phenyl-3-(trifluoromethyl)-1H-pyrazol-5-yl]benzenesulfonamide;

4-[1-(4-bromophenyl)-4-phenyl-3-(trifluoromethyl)-1H-pyrazol-5-yl]benzenesulfonamide;

4-[1-(4-iodophenyl)-4-phenyl-3-(trifluoromethyl)-1H-pyrazol-5-yl]benzenesulfonamide;

4-[1-(4-methylphenyl)-4-phenyl-3-(trifluoromethyl)-1H-pyrazol-5-yl]benzenesulfonamide;

4-[1-(4-methylthiophenyl)-4-phenyl-3-(trifluoromethyl)-1H-pyrazol-5-yl]benzenesulfonamide;

4-[1-(4-hydroxyphenyl)-4-phenyl-3-(trifluoromethyl)-1H-pyrazol-5-yl]benzenesulfonamide;

4-[1-(4-methoxyphenyl)-4-phenyl-3-(trifluoromethyl)-1H-pyrazol-5-yl]benzenesulfonamide;

4-[1-(4-nitrophenyl)-4-phenyl-3-(trifluoromethyl)-1H-pyrazol-5-yl]benzenesulfonamide;

4-[1-(4-aminophenyl)-4-phenyl-3-(trifluoromethyl)-1H-pyrazol-5-yl]benzenesulfonamide;

4-[1-(4-N-methylaminophenyl)-4-phenyl-3-(trifluoromethyl)-1H-pyrazol-5-yl]benzenesulfonamide;

4-[1-(4-N,N-dimethylaminophenyl)-4-phenyl-3-(trifluoromethyl)-1H-pyrazol-5-yl]benzenesulfonamide;

4-[1-(4-trifluoromethylphenyl)-4-phenyl-3-(trifluoromethyl)-1H-pyrazol-5-yl]benzenesulfonamide;

4-[1-(4-acetamidophenyl)-4-phenyl-3-(trifluoromethyl)-1H-pyrazol-5-yl]benzenesulfonamide;

4-[4-(4-fluorophenyl)-t-phenyl-3-(difluoromethyl)-1H-pyrazol-5-yl]benzenesulfonamide;

4-[4-(4-fluorophenyl)-1-phenyl-1H-pyrazol-5-yl]benzenesulfonamide;

4-[4-(4-fluorophenyl)-1-phenyl-3-(methyl)-1H-pyrazol-5-yl]benzenesulfonamide;

4-[4-(4-fluorophenyl)-1-phenyl-3-(cyano)-1H-pyrazol-5-yl]benzenesulfonamide;

4-[1,4-bis(4-fluorophenyl)-3-(trifluoromethyl)-1H-pyrazol-5-yl]benzenesulfonamide; and 4-[1,4-diphenyl-3-(difluoromethyl)-1H-pyrazol-5-yl]benzenesulfonamide.

Where the term "alkyl" is used, either alone or within other terms such as "haloalkyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl, and the like. The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for example, may have either a bromo, chloro or a fluoro atom within the radical. Dihalo radicals have two halo radicals or a combination of different halo radicals and polyhaloalkyl radicals have more than two of the same halo atoms or a combination of different halo radicals. Most preferred are lower haloalkyl radicals having one to about six carbon atoms. The term "alkoxy" embraces linear or branched oxy-containing radicals each having alkyl portions of one to about ten carbon atoms. Most preferred are lower alkoxy radicals having one to about six carbon atoms. The "alkoxy" radicals may be further substituted with one or more halo atoms, such as fluoro, chloro or bromo, to provide haloalkoxy or haloalkoxyalkyl radicals. The term "alkylthio" embraces radicals containing a linear or branched alkyl radical, of one to about ten carbon atoms attached to a divalent sulfur atom, such as a methylthio radical. Most preferred are lower alkylthio radicals having one to about six carbon atoms. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. Most preferred are lower alkylsulfonyl radicals having one to about six carbon atoms. The term "alkylsulfinyl" embraces radicals containing a linear or branched alkyl radical, of one to ten carbon atoms, attached to a divalent —S(=O)— atom. Most preferred are lower alkylsulfinyl radicals having one to about six carbon atoms. The terms "aminosulfonyl", "sulfamoyl" and "sulfonamide" denote a sulfonyl radical substituted with an amine radical, forming a sulfonamide (—$SO_2NH_2$). The terms "N-alkylamino" and "N,N-dialkylamino" denote amino groups which have been substituted with one alkyl radical and with two alkyl radicals, respectively. Most preferred are lower alkylamino and dialkylamino radicals having alkyl radicals of one to about six carbon atoms. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino ($CH_3C$(=O)—NH—). The term "acylaminoalkyl" embraces an alkyl radical substituted with an acylamino group, as defined above. An example of an "acylaminoalkyl" radical is (acetylamino)methyl ($CH_3C$(=O)$NHCH_2$—).

The present invention comprises a pharmaceutical composition for the treatment of inflammation and inflammation-associated disorders, such as arthritis, comprising a therapeutically-effective amount of a compound of Formula I and II in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I and II.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydriodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–III, wherein the $R^1$–$R^4$ substituents are as defined for Formula I, above, except where further noted.

Scheme I

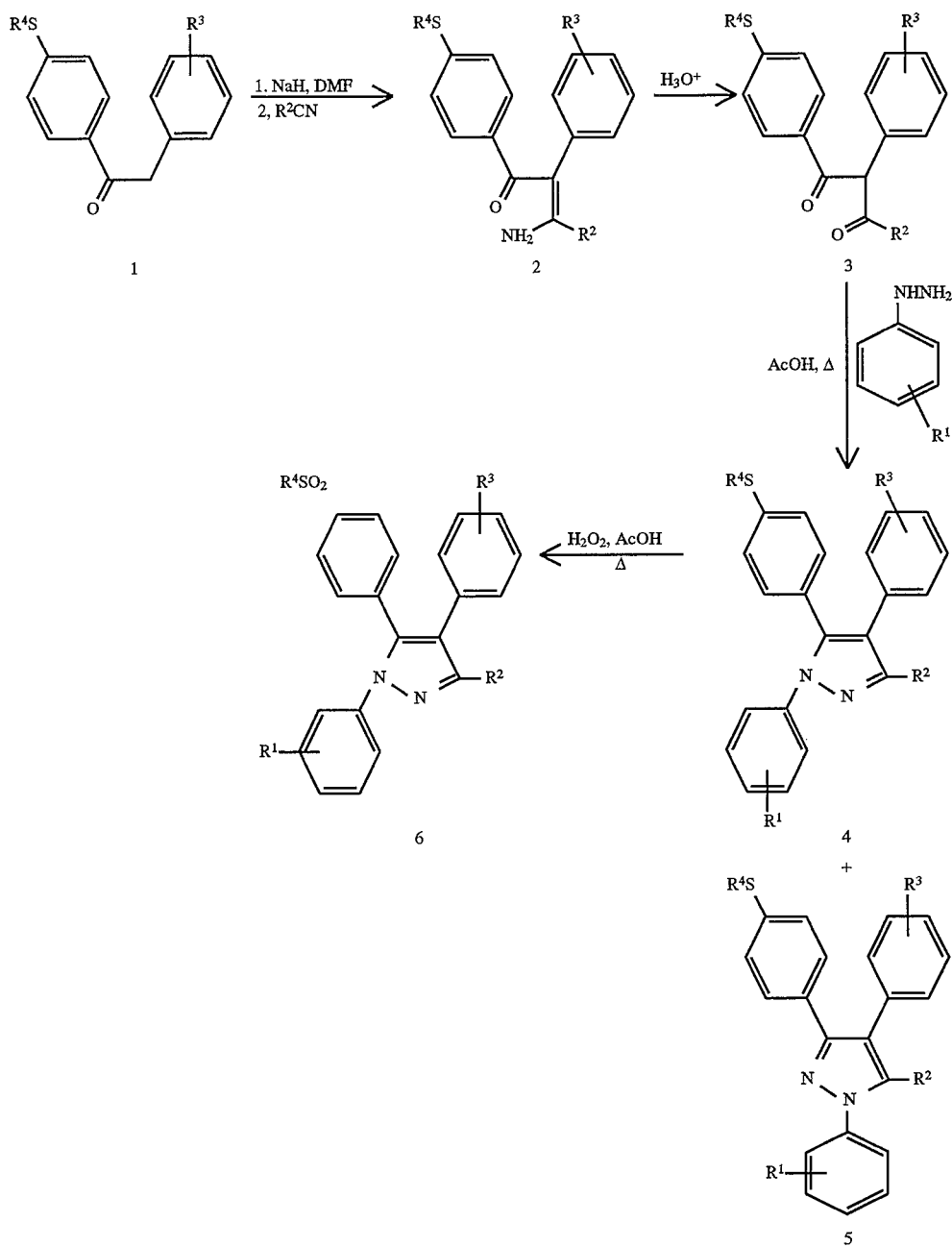

In step 1 of synthetic Scheme I, 1-[(4-alkylthio)phenyl]-2-[R³-phenyl]ethanone 1 is reacted with sodium hydride in an anhydrous aprotic solvent, such as dimethylformamide or tetrahydrofuran to form the sodium enolate. Reaction of the enolate with gaseous haloalkylnitrile yields the enamine 2. In step 2, the enamine 2 is hydrolyzed with 6N hydrochloric acid to give the 1,3-diketone 3. In step 3, reaction of the diketone 3 with a substituted or unsubstituted phenylhydrazine gives the 5-[4-(alkylthio)phenylpyrazole]4 and its position isomer 5. Separation of the desired product from its isomer can be achieved by high performance liquid chromatography (HPLC). In step 4, oxidation of pyrazole 4 with hydrogen peroxide yields 5[4-(alkylsulfonyl)phenyl]-1H-pyrazole compounds 6 embraced by Formula I.

Scheme II

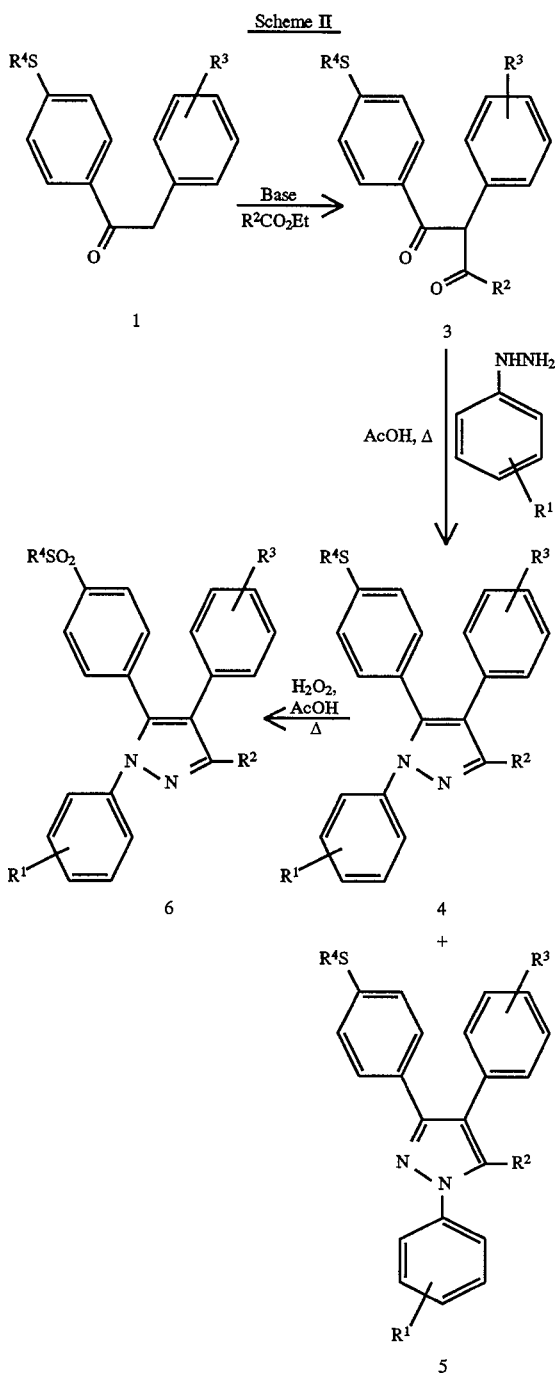

Alternatively, the compounds embraced by Formula I may be prepared, as shown in Scheme II. In step 1, 1-[(4-alkylthio)phenyl]-2-[R³-phenyl]ethanone 1is reacted with strong base, such as sodium methoxide, lithium diisopropylamide (LDA), lithium 2,2,6,6-tetramethylpiperidide or sodium bis(trimethylsilyl)amide, and an ester or ester equivalent, such as an acyl imidazole, under Claisen condensation conditions, to give the 1,3-diketone 3. In step 2, reaction of the diketone 3 with a substituted or unsubstituted phenylhydrazine gives the (5-[4-alkylthio)phenyl]-1H-pyrazole 4 and its position isomer 5. Separation of the desired product from its isomer can be achieved by high performance liquid chromatography (HPLC). In step 4, oxidation of pyrazole 4 with hydrogen peroxide yields 5-[4-(alkylsulfonyl)phenyl]-1-H-pyrazole compounds 6 embraced by Formula I.

Scheme III

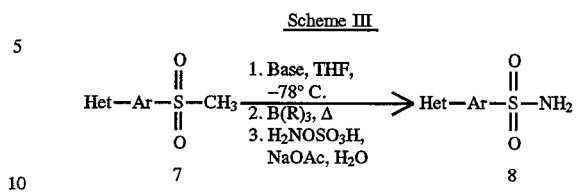

Synthetic Scheme III shows the three step procedure used to prepare sulfonamide antiinflammatory agents 8 from their corresponding methyl sulfones 7. In step one, THF solutions of the methyl sulfones 7 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxylamine-O-sulfonic acid is added to provide the corresponding sulfonamide antiinflammatory agents 8 of this invention.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

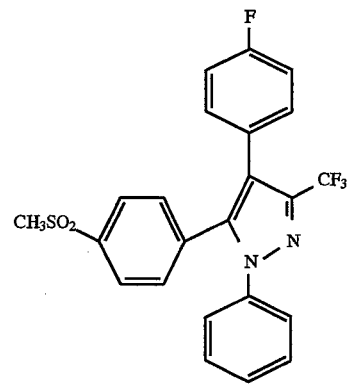

4-(4-Fluorophenyl)-5-[4-(methylsulfonyl)phenyl]-1-phenyl-3-(trifluoromethyl)pyrazole.

Step 1. Preparation of 3-amino-4,4,4-trifluoro-2-(4-fluorophnyl)-1-[4-(methylthio)phenyl]-2-buten-1-one To a mixture of 2.6 g (0.087 mol)of 80% sodium hydride oil dispersion and 10 mL of dimethylformamide (DMF) was added, under nitrogen, a solution of 21.4g (0.082 mol)of 2-(4-fluorophenyl)-1-[4-(methylthio)phenyl]ethanone in 150 ml of DMF for 30 minutes. The resulting mixture was stirred at room temperature for 1 hour. To the above mixture was passed 10 g (0.11 mol)of gaseous trifluoroacetonitrile for 40 minutes. The reaction mixture was analyzed by TLC. The reaction mixture was poured into 400 mL of water and the solid precipitate was filtered and air dried. The solid precipitate was stirred with 300 mL of ether. The insoluble material was filtered to give 6.0 g (28%) of unreacted 2-(4-fluorophenyl)-1-[4-(methylthio)phenyl]ethanone. The ether filtrate was dried over MgSO$_4$ and concentrated in vacuo. The ether filtrate was recrystallized from 5% ethyl acetate-hexane to give 12.3 g of a mixture (6:1) of 3-amino-4,4,4-trifluoro-2-(4-fluorophenyl)-1-[4-(methylthio)phenyl]-2-buten-1-one and 2-(4-fluorophenyl)-1-[4-(methylthio)phenyl]ethanone. This solid was heated with 100 mL of ether and cooled. The insoluble solid of 2-(4-fluorophenyl)-1-[4-(methylthio)phenyl]ethanone (0.5 g) was filtered. The ether filtrate was concentrated and the residue was recrystallized from 10% ethyl acetate-hexane to give 10.5 g (36%) of 3-amino-4,4,4-trifluoro-2-(4-fluorophenyl)-1-[4-(methylthio)phenyl]-2-buten-1-one, mp 122.5°–124.5° C. The combined ethyl acetate-hexane mother liquor was concentrated and the residue was purified by HPLC (10% ethyl acetate-hexane). The second fraction gave an additional 2.6 g (9%) of 3-amino-4,4,4-trifluoro-2-(4-fluorophenyl)-1-[4-(methylthio)phenyl]-2-buten-1-one after recrystallization from 5% ethyl acetate-hexane.

Step 2: Preparation of 4-(4-fluorophenyl)-3-[4-(methylthio)phenyl]-1-phenyl-5-(trifluoromethyl)pyrazole and 4-(4-fluorophenyl)-5-[4-(methylthio)phenyl]-1-phenyl-3-(trifluoromethyl)pyrazole.

A mixture of 4.0 g of product of step 1, 40 mL of ether, and 40 mL of 6 N hydrochloric acid was stirred at room temperature for 4 days. The ether layer was dried over magnesium sulfate and concentrated in vacuo to give 4.0 g of crude 2-(4-fluorophenyl)-1-[4-(methylthio)phenyl]-4,4,4-trifluoro-1,3-butandione. A mixture of 0.22 g (0.59 mmol) of this product, 0.09 g of phenylhydrazine, and 10 mL of glacial acetic acid was heated at 80 ° C. for 18 hours and poured into water. The insoluble solid was purified by HPLC (10% ethyl acetate-hexane) to give 8 mg of 4-(4-fluorophenyl)-3-[4-(methylthio)phenyl]-1-phenyl-5-(trifluoromethyl)pyrazole and 140 mg of 4-(4-fluorophenyl)-5-[4-(methylthio)phenyl]-1-phenyl-3-(trifluoromethyl)pyrazole.

Step 3: Preperation of 4-(4-fluorophenyl)-5-[4-(methylsulfonyl)phenyl]-1-phenyl-3-(trifluoromethyl)pyrazole.

To a mixture of 140 mg of 4-(4-fluorophenyl)-5-[4-(methylthio)phenyl]-1-phenyl-3-(trifluoromethyl)pyrazole and 30 mL of glacial acetic acid was added 4.1 g of 30% hydrogen peroxide. The reaction mixture was stirred at room temperature for 18 hours, heated at 80 ° C. for 8 hours, and poured into water. The insoluble solid was filtered and air dried to give 150 mg of solid, mp 201.5°–203 ° C.

BIOLOGICAL EVALUATION

Rat Carrageenan Foot Pad Edema Test

The carrageenan foot edema test was performed with materials, reagents and procedures essentially as described by Winter, et al., (Proc. soc. Exm. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, Laboratory Models for Testing NSAIDs, in Non-steroidal Anti-Inflammatory Drugs, (J. Lombardino, ed. 1985)). Results are shown in Table I.

TABLE I

RAT PAW EDEMA

| | % Inhibition @ 10 mg/kg body weight |
|---|---|
| Example 1 | 20 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

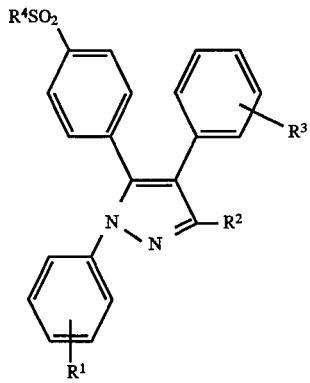

wherein $R^1$ is one or more radicals independently selected from the group hydrido, halo, $C_1$–$C_{20}$-alkyl, $C_1$–$C_{10}$-alkylthio, $C_1$–$C_{10}$-alkylsulfinyl, $C_1$–$C_{10}$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_{20}$-haloalkyl, hydroxy and $C_1$–$C_{10}$-alkoxy;

wherein $R^2$ is selected from hydrido, $C_1$–$C_{20}$-alkyl, cyano and $C_1$–$C_{20}$-haloalkyl;

wherein $R^3$ is one or more radicals independently selected from the group hydrido, halo, $C_1$–$C_{20}$-alkyl, $C_1$–$C_{10}$-alkylthio, $C_1$–$C_{10}$-alkylsulfinyl, $C_1$–$C_{10}$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_{20}$-haloalkyl, hydroxy and $C_1$–$C_{10}$-alkoxy; and wherein $R^4$ is amino; or a pharmaceutically-acceptable salt thereof.

2. Compound of claim 1 wherein $R^1$ is one or more radicals independently selected from the group hydrido, halo, $C_1$–$C_6$-alkyl, $C_1$–$C_6$-alkylthio, $C_1$–$C_6$-alkylsulfinyl, $C_1$–$C_6$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_6$-haloalkyl, hydroxy and $C_1$–$C_6$-alkoxy; wherein $R^2$ is selected from hydrido, $C_1$–$C_6$-alkyl, cyano and $C_1$–$C_6$-haloalkyl; wherein $R^3$ is one or more radicals independently selected from the group hydrido, halo, $C_1$–$C_6$-alkyl, $C_1$–$C_6$-alkylthio, $C_1$–$C_6$-alkylsulfinyl, $C_1$–$C_6$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_6$-haloalkyl, hydroxy and $C_1$–$C_6$-alkoxy; and wherein $R^4$ is amino; or a pharmaceutically-acceptable salt thereof.

3. Compound of claim 2 or a pharmaceutically-acceptable salt thereof, wherein $R^1$ is one or more groups independently selected from hydrido, methyl, ethyl, methoxy, ethoxy, methylthio, methylsulfinyl, methylsulfonyl, hydroxy, nitro, amino, N-methylamino, acetamido, trifluoromethyl, fluoro, bromo, iodo and chloro; wherein $R^2$ is selected from hydrido, cyano, methyl, ethyl, propyl, isopropyl, butyl, trifluoromethyl, difluorochloromethyl, difluoromethyl, pentafluoroethyl and heptafluoropropyl; wherein $R^3$ is one or more groups independently selected from hydrido, methyl, ethyl, methoxy, ethoxy, methylthio, methylsulfinyl, methylsulfonyl, hydroxy, nitro, amino, N-methylamino, acetamido, trifluoromethyl, fluoro, bromo, iodo and chloro; and wherein $R^4$ is amino.

4. A compound of claim 1 having the Formula II

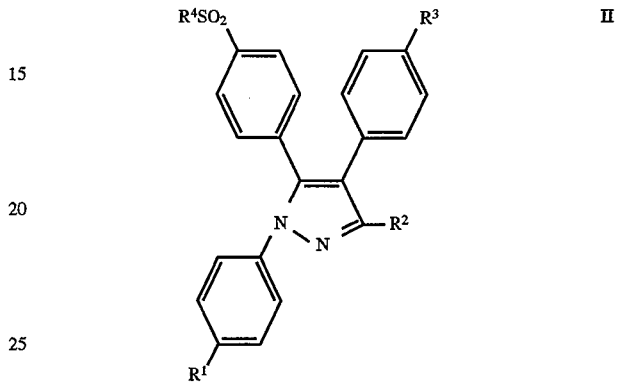

wherein $R^1$ is selected from the group hydride, halo, $C_1$–$C_{20}$-alkyl, $C_1$–$C_{10}$-alkylthio, $C_1$–$C_{10}$-alkylsulfinyl, $C_1$–$C_{10}$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_{20}$-haloalkyl, hydroxy and $C_1$–$C_{10}$-alkoxy;

wherein $R^2$ is selected from hydrido, $C_1$–$C_{20}$-alkyl, cyano and $C_1$–$C_{20}$-haloalkyl;

wherein $R^3$ is selected from the group hydrido, halo, $C_1$–$C_{20}$-alkyl, $C_1$–$C_{10}$-alkylthio, $C_1$–$C_{10}$-alkylsulfinyl, $C_1$–$C_{10}$-alkylsulfonyl, nitro, amine, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_{20}$-haloalkyl, hydroxy and $C_1$–$C_{10}$-alkoxy; and wherein $R^4$ is amino; or a pharmaceutically-acceptable salt thereof.

5. Compound of claim 4 wherein $R^1$ is selected from the group hydride, halo, $C_1$–$C_6$-alkyl, $C_1$–$C_6$-alkylthio, $C_1$–$C_6$-alkylsulfinyl, $C_1$–$C_6$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_6$-haloalkyl, hydroxy and $C_1$–$C_6$-alkoxy; wherein $R^2$ is selected from hydride, cyano, $C_1$–$C_6$-alkyl and $C_1$–$C_6$-haloalkyl; wherein $R^3$ is selected from the group hydrido, halo, $C_1$–$C_6$-alkyl, $C_1$–$C_6$-alkylthio, $C_1$–$C_6$-alkylsulfinyl, $C_1$–$C_6$-alkylsulfonyl, nitro, amino, N-mono-$C_1$–$C_{20}$-alkyl-amino, N,N-di-$C_1$–$C_{20}$-alkylamino, acylamino, acylamino-$C_1$–$C_{20}$-alkyl, $C_1$–$C_6$-haloalkyl, hydroxy and $C_1$–$C_6$-alkoxy; and wherein $R^4$ is amino; or a pharmaceutically-acceptable salt thereof.

6. Compound of claim 5 or a pharmaceutically-acceptable salt thereof, wherein $R^1$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, fluoro, bromo, iodo and chloro; wherein $R^2$ is selected from hydrido, cyano, methyl, ethyl, propyl, trifluoromethyl, difluorochloromethyl, difluoromethyl, pentafluoroethyl and heptafluoropropyl; wherein $R^3$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; and wherein $R^4$ is amino.

7. A pharmaceutical composition comprising a therapeutically-effective amount of a compound and a pharmaceutically-acceptable carrier or diluent, said compound selected from a family of compounds of Formula I

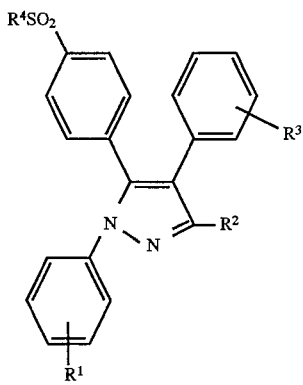

wherein $R^1$ is one or more radicals independently selected from the group hydrido, halo, $C_1$-$C_{20}$-alkyl, $C_1$-$C_{10}$-alkylthio, $C_1$-$C_{10}$-alkylsulfinyl, $C_1$-$C_{10}$-alkylsulfonyl, nitro, amino, N-mono-$C_1$-$C_{20}$-alkylamino, N,N-di-$C_1$-$C_{20}$-alkylamino, acylamino, acylamino-$C_1$-$C_{20}$-alkyl, $C_1$-$C_{20}$-haloalkyl, hydroxy and $C_1$-$C_{10}$-alkoxy;
wherein $R^2$ is selected from hydrido, $C_1$-$C_{20}$-alkyl, cyano and $C_1$-$C_{20}$-haloalkyl;
wherein $R^3$ is one or more radicals independently selected from the group hydrido, halo, $C_1$-$C_{20}$-alkyl, $C_1$-$C_{10}$-alkylthio, $C_1$-$C_{10}$-alkylsulfinyl, $C_1$-$C_{10}$-alkylsulfonyl, nitro, amino, N-mono-$C_1$-$C_{20}$-alkylamino, N,N-di-$C_1$-$C_{20}$-alkylamino, acylamino, acylamino-$C_1$-$C_{20}$-alkyl, $C_1$-$C_{20}$-haloalkyl, hydroxy and $C_1$-$C_{10}$-alkoxy; and
wherein $R^4$ is amino; or a pharmaceutically-acceptable salt thereof.

8. A pharmaceutical composition according to claim 7 comprising a therapeutically-effective amount of a compound and a pharmaceutically-acceptable carrier or diluent, said compound selected from a family of compounds of Formula II

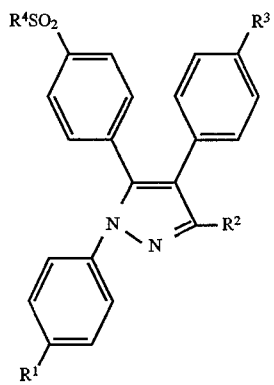

wherein $R^1$ is selected from the group hydrido, halo, $C_1$-$C_{20}$-alkyl, $C_1$-$C_{10}$-alkylthio, $C_1$-$C_{10}$-alkylsulfinyl, $C_1$-$C_{10}$-alkylsulfonyl, nitro, amino, N-mono-$C_1$-$C_{20}$-alkylamino, N,N-di-$C_1$-$C_{20}$-alkylamino, acylamino, acylamino-$C_1$-$C_{20}$-alkyl, $C_1$-$C_{20}$-haloalkyl, hydroxy and $C_1$-$C_{10}$-alkoxy;
wherein $R^2$ is selected from hydrido, $C_1$-$C_{20}$-alkyl, cyano and $C_1$-$C_{20}$-haloalkyl;

wherein $R^3$ is selected from the group hydrido, halo, $C_1$-$C_{20}$-alkyl, $C_1$-$C_{10}$-alkylthio, $C_1$-$C_{10}$-alkylsulfinyl, $C_1$-$C_{10}$-alkylsulfonyl, nitro, amino, N-mono-$C_1$-$C_{20}$-alkylamino, N,N-di-$C_1$-$C_{20}$-alkylamino, acylamino, acylamino-$C_1$-$C_{20}$-alkyl, $C_1$-$C_{20}$-haloalkyl, hydroxy and $C_1$-$C_{10}$-alkoxy; and
wherein $R^4$ is amino; or a pharmaceutically-acceptable salt thereof.

9. The composition of claim 8 wherein $R^1$ is selected from the group hydrido, halo, $C_1$-$C_6$-alkyl, $C_1$-$C_6$-alkylthio, $C_1$-$C_6$-alkylsulfinyl, $C_1$-$C_6$-alkylsulfonyl, nitro, amino, N-mono-$C_1$-$C_{20}$-alkylamino, N,N-di-$C_1$-$C_{20}$-alkylamino, acylamino, acylamino-$C_1$-$C_2$)-alkyl, $C_1$-$C_6$-haloalkyl, hydroxyl and $C_1$-$C_6$-alkoxy; wherein $R^2$ is selected from hydrido, $C_1$-$C_6$-alkyl, cyano and $C_1$-$C_6$-haloalkyl; wherein $R^3$ is selected from the group hydrido, halo, $C_1$-$C_6$-alkyl, $C_1$-$C_6$-alkylthio, $C_1$-$C_6$-alkyl sulfinyl, $C_1$-$C_6$-alkylsulfonyl, nitro, amino, N-mono-$C_1$-$C_{20}$-alkylamino, N,N-di-$C_1$-$C_{20}$-alkylamino, acylamino, acylamino-$C_1$-$C_{20}$-alkyl, $C_1$-$C_6$-haloalkyl, hydroxy and $C_1$-$C_6$-alkoxy; and wherein $R^4$ is amino; or a pharmaceutically-acceptable salt thereof.

10. Composition of claim 9, wherein $R^1$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; wherein $R^2$ is selected from hydrido, methyl, ethyl, propyl, cyano, trifluoromethyl, difluorochloromethyl, difluoromethyl, pentafluoroethyl and heptafluoropropyl; wherein $R^3$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; and wherein $R^4$ is amino; or a pharmaceutically acceptable salt thereof.

11. A method of treating inflammation or an inflammation-associated disorder in a subject, said method comprising administering to the subject having or susceptible to such inflammation or inflammation-associated disorder, a therapeutically-effective amount of a compound of Formula

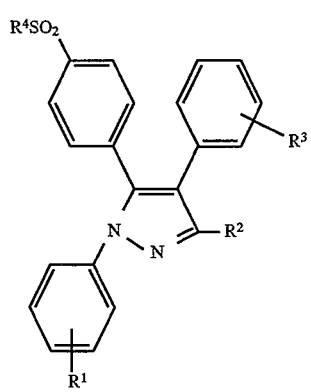

wherein $R^1$ is one or more radicals independently selected from the group hydrido, halo, $C_1$-$C_{20}$-alkyl, $C_1$-$C_{10}$-alkylthio, $C_1$-$C_{10}$-alkylsulfinyl, $C_1$-$C_{10}$-alkylsulfonyl, nitro, amino, N-mono -$C_1$-$C_{20}$-alkylamino, N,N-di -$C_1$-$C_{20}$-alkylamino, acylamino, acylamino-$C_1$-$C_{20}$-alkyl, $C_1$-$C_{20}$-haloalkyl, hydroxy and $C_1$-$C_{10}$-alkoxy;
wherein $R^2$ is selected from hydrido, $C_1$-C20 -alkyl, cyano and $C_1$-$C_{20}$-haloalkyl;
wherein $R^3$ is one or more radicals independently selected from the group hydrido, halo, $C_1$-$C_{20}$-alkyl, $C_1$-$C_{10}$- alkylthio, $C_1$–$C_{10}$-alkylsulfinyl, $C_1$–$C_{10}$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_{20}$-haloalkyl, hydroxy and $C_1$–$C_{10}$-alkoxy; and wherein $R^4$ is amino; or a pharmaceutically-acceptable salt thereof.

12. The method of claim 11 wherein the compound is of Formula II

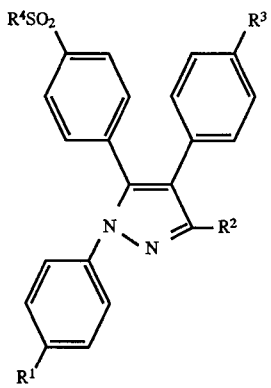

wherein $R^1$ is selected from the group hydrido, halo, $C_1$–$C_{20}$-alkyl, $C_1$–$C_{10}$-alkylthio, $C_1$–$C_{10}$-alkylsulfinyl, $C_1$–$C_{10}$-alkylsulfonyl, nitro, amino, N-mono-$C_1$–$C_{20}$-alkylamino, N,N-di-$C_1$–$C_{20}$-alkylamino, acylamino, acyl amino-$C_1$–$C_{20}$-alkyl, $C_1$–$C_{20}$-haloalkyl, hydroxy and $C_1$–$C_{10}$-alkoxy;

wherein $R^2$ is selected from hydrido, $C_1$–$C_{20}$-alkyl, cyano and $C_1$–$C_{20}$-haloalkyl;

wherein $R^3$ is selected from the group hydrido, halo, $C_1$–$C_{20}$-alkyl, $C_1$–$C_{10}$-alkylthio, $C_1$–$C_{10}$-alkylsulfinyl, $C_1$–$C_{10}$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_{20}$-haloalkyl, hydroxy and $C_1$–$C_{10}$-alkoxy; and wherein $R^4$ is amino; or a pharmaceutically-acceptable salt thereof.

13. The method of claim 12 wherein $R^1$ is selected from the group hydrido, halo, $C_1$–$C_6$-alkyl, $C_1$–$C_6$-alkylthio, $C_1$–$C_6$-alkylsulfinyl, $C_1$–$C_6$-alkylsulfonyl, nitro, amino, N-mono-$C_1$–$C_{20}$-alkylamino, N,N-di -$C_1$–$C_{20}$-alkylamino, acylamino, acylamino-$C_1$–$C_{20}$-alkyl, $C_1$–$C_6$-haloalkyl, hydroxy and $C_1$–$C_6$-alkoxy; wherein $R^2$ is selected from hydrido, $C_1$–$C_6$-alkyl, cyano and. $C_1$–$C_6$-haloalkyl; wherein $R^3$ is selected from the group hydrido, halo, $C_1$–$C_6$-alkyl, $C_1$–$C_6$-alkylthio, $C_1$–$C_6$-alkylsulfinyl, $C_1$–$C_6$-alkylsulfonyl, nitro, amino, N-mono-$C_1$–$C_{20}$-alkylamino, N,N-di-$C_1$–$C_{20}$-alkylamino, acylamino, acylamino-$C_1$–$C_{20}$-alkyl, $C_1$–$C_6$-haloalkyl, hydroxy and $C_1$–$C_6$-alkoxy; and wherein $R^4$ is amino; or a pharmaceutically-acceptable salt thereof.

14. The method of claim 13 wherein $R^1$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, bromo, iodo, fluoro and chloro; wherein $R^2$ is selected from hydrido, cyano, methyl, ethyl, propyl, trifluoromethyl, difluorochloromethyl, difluoromethyl, Dentafluoroethyl and heptafluoropropyl; wherein $R^3$ is selected from hydrido, methyl, ethyl, methoxy, ethoxy, methylthio, methylsulfinyl, methylsulfonyl, hydroxy, nitro, amino, N-methylamino, N,N-dimethylamino, acetamido, trifluoromethyl, iodo, bromo, fluoro and chloro; and wherein $R^4$ is amino; or a pharmaceutically-acceptable salt thereof.

15. The method of claim 11 for use in treatment of inflammation.

16. The method of claim 11 for use in treatment of an inflammation-associated disorder.

17. The method of claim 16 wherein the inflammation-associated disorder is arthritis.

18. The method of claim 16 wherein the inflammation-associated disorder is pain.

19. The method of claim 16 wherein the inflammation-associated disorder is fever.

20. Compound of claim 6 selected from compounds, or their pharmaceutically-acceptable salts, of the group of compounds consisting of 4-[4-(4-fluorophenyl)-1-phenyl-3-(trifluoromethyl)-1H-pyrazol-5-yl]benzenesulfonamide;

4-[4-(4-chlorophenyl)-1-phenyl-3-(trifluoromethyl)-1H-pyrazol-5-yl]benzenesulfonamide;

4-[4-(4-bromophenyl)-1-phenyl-3-(trifluoromethyl)-1H-pyrazol-5-yl]benzenesulfonamide;

4-[4-[4-iodophenyl)-1-phenyl-3-(trifluoromethyl)-1H-pyrazol-5-yl]benzenesulfonamide;

1,4-diphenyl-3-(trifluoromethyl)-1-H-pyrazol-5-yl]benzenesulfonamide;

4-[4-(4-methylphenyl)-1-phenyl-3-(trifluoromethyl)-1H-pyrazol-5-yl]benzenesulfonamide;

4-[4-(4-methylthiophenyl)-1-phenyl-3-(trifluoromethyl)-1H-pyrazol-5-yl]benzenesulfonamide;

4-[4-(4-methylsulfinylphenyl)-1-phenyl-3-(trifluoromethyl)-1H-pyrazol-5-yl]benzenesulfonamide;

4-[4-(4-hydroxyphenyl)-1-phenyl-3-(trifluoromethyl)-1H-pyrazol-5-yl]benzenesulfonamide;

4-[4-(-methoxyphenyl)-1-phenyl-3-(trifluoroethyl)-1H-pyrazol-5-yl]benzenesulfonamide;

4-[4-(4-nitrophenyl)-1-phenyl-3-(trifluoroethyl)-1H-pyrazol-5-yl]benzenesulfonamide;

4-[4-(4-aminophenyl)-1-phenyl-3-(trifluorormethyl)-1H-pyrazol-5-yl]benzenesulfonamide;

4-[4-(4-N-methylaminophenyl)-1-phenyl-3-(trifluoromethyl)-1H-pyrazol-5-yl]benzenesulfonamide;

4-[4-(4-N,N-dimethylaminophenyl)-1-phenyl-3-(trifluoromethyl)-1H-pyrazol-5-yl]benzenesulfonamide;

4-[4-(4-trifluoromethylphenyl)-1-phenyl-3-(trifluoromethyl)-1H-pyrazol-5-yl]benzenesulfonamide;

4-[4-(4-acetamidophenyl)-1-phenyl-3-(trifluoromethyl)-1H-pyrazol-5-yl]benzenesulfonamide;

4-[4-(4-[N-acetylamino]methylphenyl)-1-phenyl-3-(trifluoromethyl)-1H-pyrazol-5-yl]benzenesulfonamide;

4-[1-(4-fluorophenyl)-4-phenyl-3-(trifluoromethyl)-1H-pyrazol-5-yl]benzenesulfonamide;

4-[1-(4-chlorophenyl)-4-phenyl-3-(trifluoromethyl)-1H-pyrazol-5-yl]benzenesulfonamide;

4-[1-(4-bromophenyl)-4-phenyl-3-(trifluoromethyl)-1H-pyrazol-5-yl]benzenesulfonamide;

4-[1-(4-iodophenyl)-4-phenyl-3-(trifluoromethyl)-1H-pyrazol-5-yl]benzenesulfonamide;

4-[1-(4-methylphenyl)-4-phenyl-3-(trifluoromethyl)-1H-pyrazol-5-yl]benzenesulfonamide;

4-[1-(4-methylthiophenyl)-4-phenyl-3-(trifluoromethyl)-1H-pyrazol-5-yl]benzenesulfonamide;

4-[1-(4-hydroxyphenyl)-4-phenyl-3-(trifluoromethyl)-1H-pyrazol-5-yl]benzenesulfonamide;

4-[1-(4-methoxyphenyl)-4-phenyl-3-(trifluoromethyl)-1H-pyrazol-5-yl]benzenesulfonamide;

4-[1-(4-nitrophenyl)-4-phenyl-3-(trifluoromethyl)-1H-pyrazol-5-yl]benzenesulfonamide;

4-[1-(4-aminophenyl)-4-phenyl-3-(trifluoromethyl)-1H-pyrazol-5-yl]benzenesulfonamide;

4-[1-(4-N-methylaminophenyl)-4-phenyl-3-(trifluoromethyl)-1H-pyrazol-5-yl]benzenesulfonamide;

4-[1-(4-N,N-dimethylaminophenyl)-4-phenyl-3-(trifluoromethyl)-1H-pyrazol-5-yl]benzenesulfonamide;

4-[1-(4-trifluoromethylphenyl)-4-phenyl-3-(trifluoromethyl)-1H-pyrazol-5-yl]benzenesulfonamide;

4-[1-(4-acetamidophenyl)-4-phenyl-3-(trifluoromethyl)-1H-pyrazol-5-yl]benzenesulfonamide;

4-[4-(4-fluorophenyl)-1-phenyl-3-(difluoromethyl)-1H-pyrazol-5-yl]benzenesulfonamide;

4-[4-(4-fluorophenyl)-1-phenyl-1H-pyrazol-5-yl]benzenesulfonamide;

4-[4-(4-fluorophenyl)-1-phenyl-3-(methyl)-1H-pyrazol-5-yl]benzenesulfonamide;

4-[4-(4-fluorophenyl)-1-phenyl-3-(cyano)-1H-pyrazol-5-yl]benzenesulfonamide;

4-[1,4-bis(4-fluorophenyl)-3-(trifluoromethyl)-1H-pyrazol-5-yl]benzenesulfonamide; and 4-[1,4-diphenyl-3-(difluoromethyl)-1H-pyrazol-5-yl]benzenesulfonamide.

21. Composition of claim 10 wherein said compound is selected from compounds, and their pharmaceutically-acceptable salts, of the group of compounds consisting of 4-[4-(4-fluorophenyl)-1-phenyl-3-(trifluoromethyl)-1H-pyrazol-5-yl]benzenesulfonamide;

4-[4-(4-chlorophenyl)-1-phenyl-3-(trifluoromethyl)-1H-pyrazol-5-yl]benzenesulfonamide;

4-[4-(4-bromophenyl)-1-phenyl-3-(trifluoromethyl)-1H-pyrazol-5-yl]benzenesulfonamide;

4-[4-(4-iodophenyl)-1-phenyl-3-(trifluoromethyl)-1H-pyrazol-5-yl]benzenesulfonamide;

1,4-diphenyl-3-(trifluoromethyl)-1H-pyrazol-5-yl]benzenesulfonamide;

4-[4-(4-methylphenyl)-1-phenyl-3-(trifluoromethyl)-1H-pyrazol-5-yl]benzenesulfonamide;

4-[4-(4-methylthiophenyl)-1-phenyl-3-(trifluoromethyl)-1H-pyrazol-5-yl]benzenesulfonamide;

4-[4-(4-methylsulfinylphenyl)-1-phenyl-3-(trifluoromethyl)-1H-pyrazol-5-yl]benzenesulfonamide;

4-[4-(4-hydroxyphenyl)-1-phenyl-3-(trifluoromethyl)-1H-pyrazol-5-yl]benzenesulfonamide;

4-[4-(4-methoxyphenyl)-1-phenyl-3-(trifluoromethyl)-1H-pyrazol-5-yl]benzenesulfonamide;

4-[4-(4-nitrophenyl)-1-phenyl-3-(trifluoromethyl)-1H-pyrazol-5-yl]benzenesulfonamide;

4-[4-(4-aminophenyl)-1-phenyl-3-(trifluoromethyl)-1H-pyrazol-5-yl]benzenesulfonamide;

4-[4-(4-N-methylaminophenyl)-1-phenyl-3-(trifluoromethyl)-1H-pyrazol-5-yl]benzenesulfonamide;

4-[4-(4-N,N-dimethylaminophenyl)-1-phenyl-3-(trifluoromethyl)-1H-pyrazol-5-yl]benzenesulfonamide;

4-[4-(4-trifluoromethylphenyl)-1-phenyl-3-(trifluoromethyl)-1H-pyrazol-5-yl]benzenesulfonamide;

4-[4-(4-acetamidophenyl)-1-phenyl-3-(trifluoromethyl)-1H-pyrazol-5-yl]benzenesulfonamide;

4-[4-(4-[N-acetylamino]methylphenyl)-1-phenyl-3-(trifluoromethyl)-1H-pyrazol-5-yl]benzenesulfonamide;

4-[1-(4-fluorophenyl)-4-phenyl-3-(trifluoromethyl)-1H-pyrazol-5-yl]benzenesulfonamide;

4-[1-(4-chlorophenyl)-4-phenyl-3-(trifluoromethyl)-1H-pyrazol-5-yl]benzenesulfonamide;

4-[1-(4-bromophenyl)-4-phenyl-3-(trifluoromethyl)-1H-pyrazol-5-yl]benzenesulfonamide;

4-[1-(4-iodophenyl)-4-phenyl-3-(trifluoromethyl)-1H-pyrazol-5-yl]benzenesulfonamide;

4-[1-(4-methylphenyl)-4-phenyl-3-(trifluoromethyl)-1H-pyrazol-5-yl]benzenesulfonamide;

4-[1-(4-methylthiophenyl)-4-phenyl-3-(trifluoromethyl)-1H-pyrazol-5-yl]benzenesulfonamide;

4-[1-(4-hydroxyphenyl)-4-phenyl-3-(trifluoromethyl)-1H-pyrazol-5-yl]benzenesulfonamide;

4-[1-(4-methoxyphenyl)-4-phenyl-3-(trifluoromethyl)-1H-pyrazol-5-yl]benzenesulfonamide;

4-[1-(4-nitrophenyl)-4-phenyl-3-(trifluoromethyl)-1H-pyrazol-5-yl]benzenesulfonamide;

4-[1-(4-aminophenyl)-4-phenyl-3-(trifluoromethyl)-1H-pyrazol-5-yl]benzenesulfonamide;

4-[1-(4-N-methylaminophenyl)-4-phenyl-3-(trifluoromethyl)-1H-pyrazol-5-yl]benzenesulfonamide;

4-[1-(4-N,N-dimethylaminophenyl)-4-phenyl-3-(trifluoromethyl)-1H-pyrazol-5-yl]benzenesulfonamide;

4-[1-(4-trifluoromethylphenyl)-4-phenyl-3-(trifluoromethyl)-1H-pyrazol-5-yl]benzenesulfonamide;

4-[1-(4-acetamidophenyl)-4-phenyl-3-(trifluoromethyl)-1H-pyrazol-5-yl]benzenesulfonamide;

4-[4-(4-fluorophenyl)-1-phenyl-3-(difluoromethyl)-1H-pyrazol-5-yl]benzenesulfonamide;

4-[4-(4-fluorophenyl)-1-phenyl-1H-pyrazol-5-yl]benzenesulfonamide;

4-[4-(4-fluorophenyl)-1-phenyl-3-(methyl)-1H-pyrazol-5-yl]benzenesulfonamide;

4-[4-(4-fluorophenyl)-1-phenyl-3-(cyano)-1H-pyrazol-5-yl]benzenesulfonamide;

4-[1,4-bis(4-fluorophenyl)-3-(trifluoromethyl)-1H-pyrazol-5-yl]benzenesulfonamide; and 4-[1,4-diphenyl-3-(difluoromethyl)-1H-pyrazol-5-yl]benzenesulfonamide.

22. The method of claim 14 wherein said compound is selected from compounds, and their pharmaceutically-acceptable salts, of the group of compounds consisting of 4-[4-(4-fluorophenyl)-1-phenyl-3-(trifluoromethyl)-1H-pyrazol-5-yl]benzenesulfonamide;

4-[4-(4-chlorophenyl)-1-phenyl-3-(trifluoromethyl)-1H-pyrazol-5-yl]benzenesulfonamide;

4-[4-(4-bromophenyl)-1-phenyl-3-(trifluoromethyl)-1H-pyrazol-5-yl]benzenesulfonamide;

4-[4-(4-iodophenyl)-1-phenyl-3-(trifluoromethyl)-1H-pyrazol-5-yl]benzenesulfonamide;

1,4-diphenyl-3-(trifluoromethyl)-1H-pyrazol-5-yl]benzenesulfonamide;

4-[4-(4-methylphenyl)-1-phenyl-3-(trifluoromethyl)-1H-pyrazol-5-yl]benzenesulfonamide;

4-[4-(4-methylthiophenyl)-1-phenyl-3-(trifluoromethyl)-1H-pyrazol-5-yl]benzenesulfonamide;

4-[4-(4-methylsulfinylphenyl)-1-phenyl-3-(trifluoromethyl)-1H-pyrazol-5-yl]benzenesulfonamide;

4-[4-(4-hydroxyphenyl)-1-phenyl-3-(trifluoromethyl)-1H-pyrazol-5-yl]benzenesulfonamide;

4-[4-(4-methoxyphenyl)-1-phenyl-3-(trifluoromethyl)-1H-pyrazol-5-yl]benzenesulfonamide;

4-[4-(4-nitrophenyl)-1-phenyl-3-(trifluoromethyl)-1H-pyrazol-5-yl]benzenesulfonamide;

4-[4-(4-aminophenyl)-1-phenyl-3-[trifluoromethyl)-1H-pyrazol-5-yl]benzenesulfonamide;

4-[4-(4-N-methylaminophenyl)-1-phenyl-3-(trifluoromethyl)-1H-pyrazol-5-yl]benzenesulfonamide;

4-[4-(4-N,N-dimethylaminophenyl)-1-phenyl-3-(trifluoromethyl)-1H-pyrazol-5-yl]benzenesulfonamide;

4-[4-(4-trifluoromethylphenyl)-1-phenyl-3-(trifluoromethyl)-1H-pyrazol-5-yl]benzenesulfonamide;

4-[4-(4-acetamidophenyl)-1-phenyl-3H-pyrazol-5-yl]benzenesulfonamide;

4-[4-(4-[N-acetylamino]methylphenyl)-1-phenyl-3-(trifluoromethyl)-1H-pyrazol-5-yl]benzenesulfonamide;

4-[1-(4-fluorophenyl)-4-phenyl-3-(trifluoromethyl)-1H-pyrazol-5-yl]benzenesulfonamide;

4-[1-(4-chlorophenyl)-4-phenyl-3-(trifluoromethyl)-1H-pyrazol-5-yl]benzenesulfonamide;

4-[1-(4-bromophenyl)-4-phenyl-3-(trifluoromethyl)-1H-pyrazol-5-yl]benzenesulfonamide;

4-[1-(4-iodophenyl)-4-phenyl-3-(trifluoromethyl)-1H-pyrazol-5-yl]benzenesulfonamide;

4-[1-(4-methylphenyl)-4-phenyl-3-(trifluoromethyl)-1H-pyrazol-5-yl]benzenesulfonamide;

4-[1-(4-methylthiophenyl)-4-phenyl-3-(trifluoromethyl)-1H-pyrazol-5-yl]benzenesulfonamide;

4-[1-(4-hydroxyphenyl)-4-phenyl-3-(trifluoromethyl)-1H-pyrazol-5-yl]benzenesulfonamide;

4-[1-(4-methoxyphenyl)-4-phenyl-3-(trifluoromethyl)-1H-pyrazol-5-yl]benzenesulfonamide;

4-[1-(4-nitrophenyl)-4-phenyl-3-(trifluoromethyl)-1H-pyrazol-5-yl]benzenesulfonamide;

4-[1-(4-aminophenyl)-4-phenyl-3-(trifluoromethyl)-1H-pyrazol-5-yl]benzenesulfonamide;

4-[1-(4-N-methyl aminophenyl)-4-phenyl-3-(trifluoromethyl)-1H-pyrazol-5-yl]benzenesulfonamide;

4-[1-(4-N,N-dimethylaminophenyl)-4-phenyl-3-(trifluoromethyl)-1H-pyrazol-5-yl]benzenesulfonamide;

4-[1-(4-trifluoromethylphenyl)-4-phenyl-3-(trifluoromethyl)-1H-pyrazol-5-yl]benzenesulfonamide;

4-[1-(4-acetamidophenyl)-4-phenyl-3-(trifluoromethyl)-1H-pyrazol-5-yl]benzenesulfonamide;

4-[4-(4-fluorophenyl)-1-phenyl-3-(difluoromethyl)-1H-pyrazol-5-yl]benzenesulfonamide;

4-[4-(4-fluorophenyl)-1-phenyl-1H-pyrazol-5-yl]benzenesulfonamide;

4-[4-(4-fluorophenyl)-1-phenyl-3-(methyl)-1H-pyrazol-5-yl]benzenesulfonamide;

4-[4-(4-fluorophenyl)-1-thienyl-3-(cyano)-1H-pyrazol-5-yl]benzenesulfonamide;

4-[1,4-bis(4-fluorophenyl)-3-(trifluoromethyl)-1H-pyrazol-5-yl]benzenesulfonamide; and 4-[1,4-diphenyl-3-(difluoromethyl)-1H-pyrazol-5-yl]benzenesulfonamide.

\* \* \* \* \*